US006587701B1

(12) United States Patent
Stranc et al.

(10) Patent No.: US 6,587,701 B1
(45) Date of Patent: Jul. 1, 2003

(54) METHOD OF ASSESSING TISSUE VIABILITY USING NEAR-INFRARED SPECTROSCOPY

(76) Inventors: Miroslaw F. Stranc, 295 Lindsay Street, Winnipeg Manitoba (CA), R3N 1H2; Michael G. Sowa, 435 Ellice Avenue, Winnipeg Manitoba (CA), R3B 1Y6; Henry H. Mantsch, 435 Ellice Avenue, Winnipeg Manitoba (CA), R3B 1Y6

( * ) Notice: Subject to any disclaimer, the term of this patent is extended or adjusted under 35 U.S.C. 154(b) by 76 days.

(21) Appl. No.: 09/402,348
(22) PCT Filed: Apr. 2, 1998
(86) PCT No.: PCT/CA98/00292
§ 371 (c)(1),
(2), (4) Date: Feb. 17, 2000
(87) PCT Pub. No.: WO98/44839
PCT Pub. Date: Oct. 15, 1998

(51) Int. Cl.[7] .................................................. A61B 5/00
(52) U.S. Cl. ........................ 600/310; 600/473; 600/476; 600/322
(58) Field of Search ................................. 600/309–310, 600/322–324, 407, 473, 475–477; 356/39–41

(56) References Cited

U.S. PATENT DOCUMENTS

| | | | |
|---|---|---|---|
| 5,701,902 A | * 12/1997 | Vari et al. | 600/473 |
| 5,813,987 A | * 9/1998 | Modell et al. | 600/473 |
| 5,830,133 A | * 11/1998 | Osten et al. | 600/322 |
| 5,865,738 A | * 2/1999 | Morcos et al. | 600/365 |
| 5,954,053 A | * 9/1999 | Chance et al. | 600/310 |
| 5,987,351 A | * 11/1999 | Chance | 600/473 |
| 6,196,226 B1 | * 3/2001 | Hochman et al. | 600/407 |

OTHER PUBLICATIONS

Irwin, M.S. et al, "Near infrared spectroscopy: a non–invasive monitor of perfusion and oxygenation within the microcirculation of limbs and flaps", 1995, British Journal of Plastic Surgery, vol. 48, pp. 14–22.*

* cited by examiner

Primary Examiner—Eric F. Winakur
Assistant Examiner—Matthew Kremer
(74) Attorney, Agent, or Firm—Michael R. Williams; Adrian D. Battison; Ryan W. Dupuis

(57) ABSTRACT

Prolonged and severe tissue hypoxia results in tissue necrosis in pedicled flaps. We demonstrate the potential of near-infrared spectroscopy for predicting viability of compromised tissue portions. This approach clearly identifies tissue regions with low oxygen supply, and also the severity of this challenge, in a rapid and non-invasive manner, with a high degree of reproducibility. Tissues remaining below a certain hemoglobin oxygen saturation threshold (oxygen saturation index<1) for prolonged periods (>6 h) became increasingly dehydrated, eventually becoming visibly necrotic. Tissues above this threshold (oxygen saturation index>1), despite being significantly hypoxic relative to the pre-elevation saturation values, remained viable over the 72 h post-elevation monitoring period. The magnitude of the drop in tissue oxygen saturation, as observed immediately following surgery, correlated with the final clinical outcome of the flap tissue. These results indicate the potential of near infrared spectroscopy and imaging to monitor tissue oxygenation status and assess tissue viability following reconstructive surgery. Early, nonsubjective detection of poor tissue oxygenation following surgery increases the likelihood that intervention aimed at saving the tissue will be successful.

16 Claims, 24 Drawing Sheets

Factor Number

A. Raw
 B. Median Filtered
 C. Log Residual
 D. Statistically Scaled

METHOD OF ASSESSING TISSUE VIABILITY USING NEAR-INFRARED SPECTROSCOPY

The present invention relates generally to a method of determining tissue viability. More specifically, the present invention relates to a non-invasive method of determining tissue viability using visible and near-infrared spectroscopy.

BACKGROUND OF THE INVENTION

In surgery, the ability to determine whether or not a tissue will survive is of paramount importance. This is particularly true in plastic surgery where efforts to develop a reliable method to predict skin flap viability are ongoing. It is therefore not surprising that efforts to develop a reliable method to predict tissue viability go back to the very beginnings of plastic surgery. Clinical assessment, based on observations of color, temperature and capillary perfusion have always been, and remain, the basis of good management. However, the clinical signs which arise as a consequence of poor blood perfusion along the flap become evident only after several hours of compromised perfusion. Prolonged and severe deprivation of oxygen and other nutrients to the tissues results in irreversible tissue damage leading to necrosis and loss of tissue. Early, nonsubjective detection of poor tissue oxygenation following surgery increases the likelihood that intervention aimed at saving the tissue will be successful. As a consequence, a variety of methods have evolved over the years to augment clinical judgement. Broadly speaking, these methods fall into two categories: those that are based on an assessment of blood flow within tissues and those that examine the cellular metabolism within tissues.

Early studies depended on the use of pharmacological agents to assess blood flow (Hynes, 1948, *Br J Plast Surg* 1:159–171; Conway et al, 1951, *Surg Gynecol Obstet* 93:185–189). It was soon realized that the use of pharmacologic agents gave inconsistent results which were difficult to interpret.

Later, vital dye studies and the use of radioisotopes added to our knowledge (Dingwall and Lord, 1943, *Bull Johns Hopkins Hosp* 73:129–134; Kety, 1949, *Am Heart J* 38:321–328). Also, fluorescein dye or other labelled tracer measurements of blood flow were necessarily invasive procedures and the invasiveness of the procedure coupled with prolonged washout times limited the frequency with which these methods could be applied to the site of interest.

More recently, Doppler evaluation of blood flow (Swartz et al, 1988, *Plast Reconst Surg* 81:149–161), assessment of oxygen transport (Hjortdal et al, 1990, *Scand J Plast Reconstr Surg Hand Surg* 24:27–30) and sophisticated monitoring of tissue temperature (Kaufman et al, 1987, *Ann Plast Surg* 19:34–41) held promise. Laser Doppler velocimetry had the advantage of being a non-invasive method. However, it only measured the blood flow within a small volume of tissue, and microvascular heterogeneity rendered the method prone to errors: motion of the probe during measurement and poor probe placement reproducibility both led to poor reproducibility. In addition, the recognition of arteriovenous shunting, where blood flow bypasses the capillary bed resulting in non-nutrient flow, reduced the value of a strictly blood flow-based investigation. Blood flow methods primarily address the issue of oxygen delivery, but provide little information on cellular utilization.

Finally, the most recent advances examine the metabolic status of tissues using magnetic resonance imaging (Cheung et al, 1994, *Magn Reson Med* 32:572–578) and infrared spectroscopy (Irwin et al, 1995, *Br J Plast Surg* 48:14–22). Magnetic resonance spectroscopy can provide information on the metabolic status of skin flaps at a cellular level (Cheung, 1994), but the extended measurement times, high costs, and limited portability render the method clinically impractical.

Regarding infrared spectroscopy, U.S. Pat. No. 3,638,640 to Shaw, for example, teaches disposing radiation sources and detectors about the ear of a patient and measuring the intensity of radiation passing therethrough. The logarithms of the detector responses are then combined linearly to yield an indication of oxygen saturation in the blood based on the ratio of concentration of oxyhemoglobin to total hemoglobin in the patient's ear. Clearly, this device is limited in that it provides information only on the oxygenation level of the blood.

U.S. Pat. Nos. 4,223,680 and 4,281,645, both to Jöbsis, teach a method and art apparatus for continuous in vivo monitoring of metabolism in a body organ using near infrared spectroscopy. Specifically, oxygen sufficiency in an organ is measured based on the absorbance characteristics of cytochrome a, $a_3$. However, this apparatus is arranged to measure changes and trends in metabolism and not tissue viability.

U.S. Pat. No. 5,074,306 to Green teaches a method for measuring burn depth comprising administering a fluorescent compound to the skin burn and exciting the fluorescent compound with infrared light. The amount of fluorescence detected at the skin burn compared to the adjacent unburned skin provides an indication as to the depth of the burn. However, as with fluorescein dye and other vital dyes discussed above, this method is invasive and may harm the compromised tissue or the surrounding tissue. Furthermore, the device is used to determine the depth of the burn in the tissue, not the viability of the tissue.

U.S. Pat. No. 5,497,770 to Morcos teaches an apparatus for measuring dynamic oxidative metabolism in compromised myocardium. Specifically, Morcos teaches injecting one or more metabolic substrates in a region of the compromised myocardium and collecting near infrared spectra over time using a probe inserted into the region of interest. The collected data is then used to determine whether a metabolic pathway cascade or a transmembrane ionic potential are intact, which is in turn used to provide an indication as to the viability of the cells. Clearly, this method is too invasive for use with damaged tissue, as it requires both the insertion of a probe below the surface of the tissue and injection of one or more metabolic substrates into the tissue.

Irwin (Irwin, 1995) teaches a method and a device for continuously monitoring concentration changes in oxyhemoglobin, deoxyhemoglobin and total hemoglobin. However, the method is limited in that the device must be mounted onto the surface of the tissue being examined and, as a result, is prone to interference if the probe is removed and subsequently replaced on the suspect tissue. Furthermore, as noted above, the method and the device are designed to measure trends meaning that hemoglobin levels must be continuously monitored in order for useful data to be collected.

It is therefore not surprising that a recent survey amongst microsurgeons showed a lack of uniformity in the use of monitoring devices to assess viability of transplanted tissue (Neligan, 1993, *Microsurgery* 14:162–164). The ideal test to predict skin viability should be quick and simple to perform, accurate and reproducible, inexpensive, non-invasive, cause little or no patient discomfort and should not alter the basic physiology of the tissue.

SUMMARY OF THE INVENTION

According to the invention there is provided a method of assessing tissue viability of a patient comprising:

accessing a portion of tissue of the patient wherein the communication of fluids between the portion and a main body of the patient is compromised such that the viability of the tissue portion, that is, survival or outcome of the tissue portion, is in question;

locating a probe at the tissue portion;

collecting from the probe at least one spectrum of visible and near infra-red light from the tissue portion;

analyzing the spectrum to generate data related to the viability of the tissue portion, wherein viability is related to the outcome of the tissue portion in the absence of any intervention aimed at altering said outcome;

and using the data to make a determination of the viability of the tissue portion, wherein sufficient spectral points and data are collected so that the determination of the viability of the tissue may be made from a single spectrum. As a result, an indication as to tissue viability is immediately available, without the need to take multiple readings and analyze trends. This in turn means that corrective measures can be taken more quickly, thereby improving the likelihood of tissue survival.

The tissue portion may form a portion of the body which is damaged. The damage may be caused by burning or freezing.

The tissue portion may be attached to the main body portion by rejoining severed blood vessels, thereby compromising the communication of fluid from the main body portion to the tissue portion.

Preferably, the data related to the viability of the tissue portion comprises data on oxygenation of the tissue portion. The data on the oxygenation of the tissue portion may comprise comparing levels of deoxyhemoglobin and oxyhemoglobin. The levels of deoxyhemoglobin and oxyhemoglobin may be compared by measuring the ratio of absorbance at a wavelength between 790–810 nm to absorbance at a wavelength between 740–780 nm. More specifically, the levels of deoxyhemoglobin and oxyhemoglobin may be compared by measuring the ratio of absorbance at 800 nm to absorbance at 760 nm.

The method may include the steps of removing the probe, subsequently relocating the probe proximal to the tissue portion, collecting from the probe at least one spectrum of visible and near infra-red light from the tissue portion, analyzing the spectrum to generate data related to the viability of the tissue portion and comparing the data from the first analysis with the data from the subsequent analysis. Thus, the above-described method may be used to examine tissue viability over time without the need for continuous monitoring.

The method may include the steps of removing the probe, subsequently relocating the probe proximal to a second tissue portion, collecting from the probe at least one spectrum of visible and near infra-red light from the second tissue portion, analyzing the spectrum to generate data related to the viability of the second tissue portion and comparing the data from the tissue portion with the data from the second tissue portion. As the above-described method does not require the monitoring of trends, the probe can be removed from the patient and used to examine another tissue portion.

The second tissue portion may be of a second patient.

Preferably, the comparison of the data involves comparing the spectra at at least one reference point. The reference point may comprise a wavelength at which the absorption coefficient of deoxyhemoglobin and oxyhemoglobin is approximately equal, for example, at a wavelength between 790–810 nm. The wavelength may be 800 nm.

Preferably, the data related to the viability of the tissue portion comprises data on hydration of the tissue portion. The data on the hydration of the tissue portion may be obtained by measuring the water content of the tissue portion, for example, by measuring the ratio of absorbance at a wavelength between 960–1080 nm to absorbance at 900 nm. The ratio of absorbance may be taken at 980 nm to 900 nm.

Preferably, the data related to the viability of the tissue portion comprises data on both hydration and oxygenation of the tissue portion. The data on the oxygenation of the tissue may be obtained by measuring the ratio of absorbance at a wavelength between 790–810 nm to absorbance at a wavelength between 740–780 nm and the data on the hydration of the tissue portion may be obtained by measuring the ratio of absorbance at a wavelength between 900–1080 nm to absorbance at 900 nm. The data on the oxygenation of the tissue may be obtained by measuring the ratio of absorbance at 800 nm to absorbance at 760 nm and the data on the hydration of the tissue portion may be obtained by measuring the ratio of absorbance at 980 nm to absorbance at 900 nm.

The probe may be located at least 1 mm away from the tissue portion. That is, the probe does not have to be mounted or attached to the damaged tissue to collect spectrum data.

Preferably, the spectrum is collected in the absence of added metabolic substrate.

760 nm attenuation ratio) at five selected sites along the reverse McFarlane dorsal skin flap (n=9) immediately prior to surgery (t=0) and within 1, 6 and 12 hours post-elevation.

Figure 2:
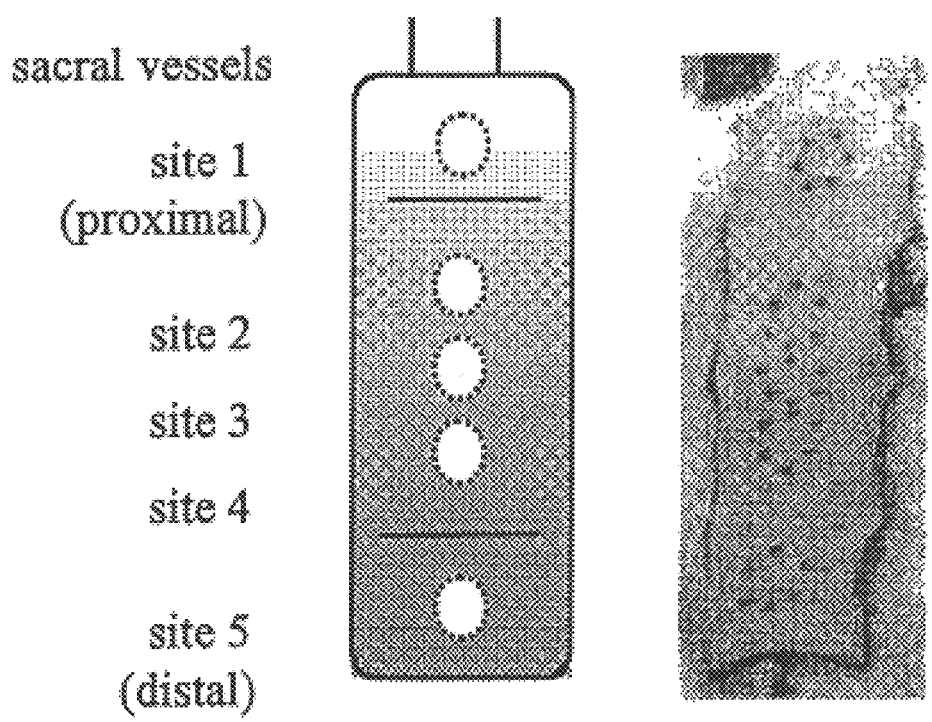
FIG. 2, left panel, is a schematic illustration of the dorsal reversed McFarlane skin flap model in the rat and the right panel is a gray-scale image of the flap.
Figure 8:
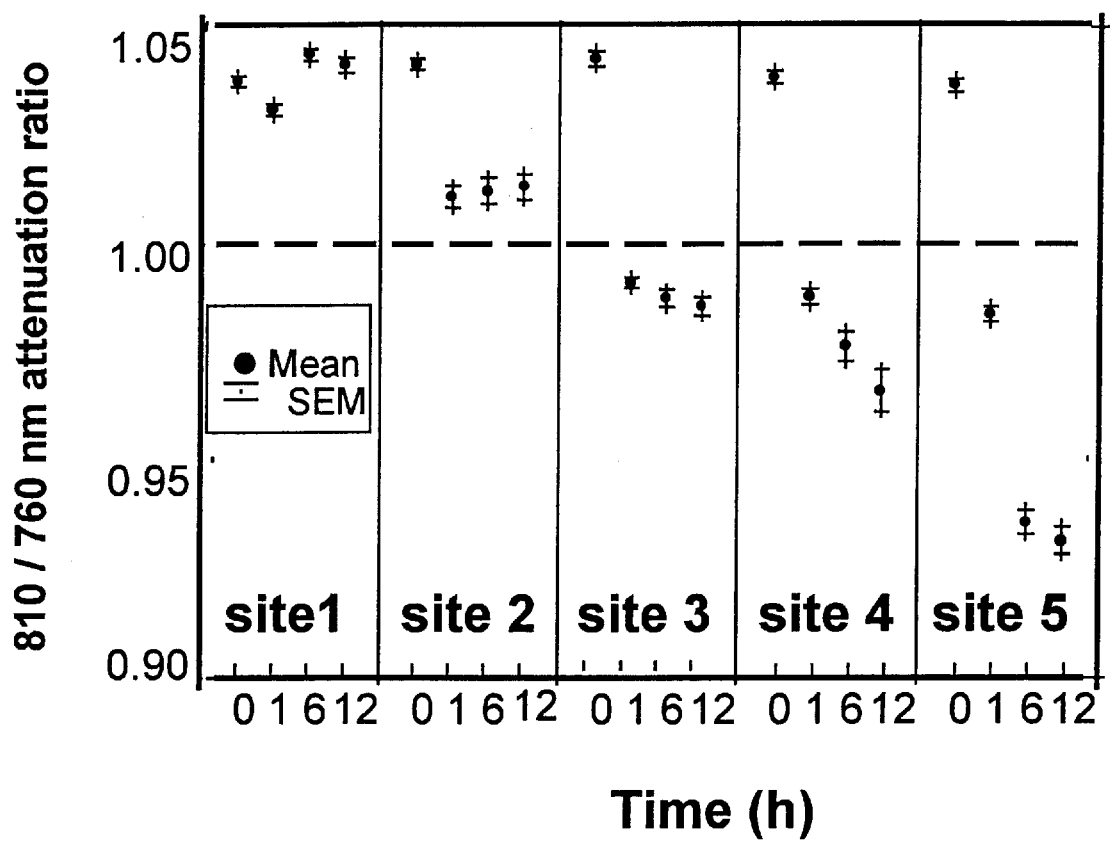

FIG. 8 is oxygen saturation index based on the 810/760 nm attenuation (OD) ratio with the mean and standard error of the mean of the attenuation ratio pooled over n=9 skin flaps presented for the five skin flap measurement sites shown in FIG. 2 immediately prior to surgery (t=0 hours) 1, 6 and 12 hours following elevation of the reversed McFarlane skin flap.

Figure 3:
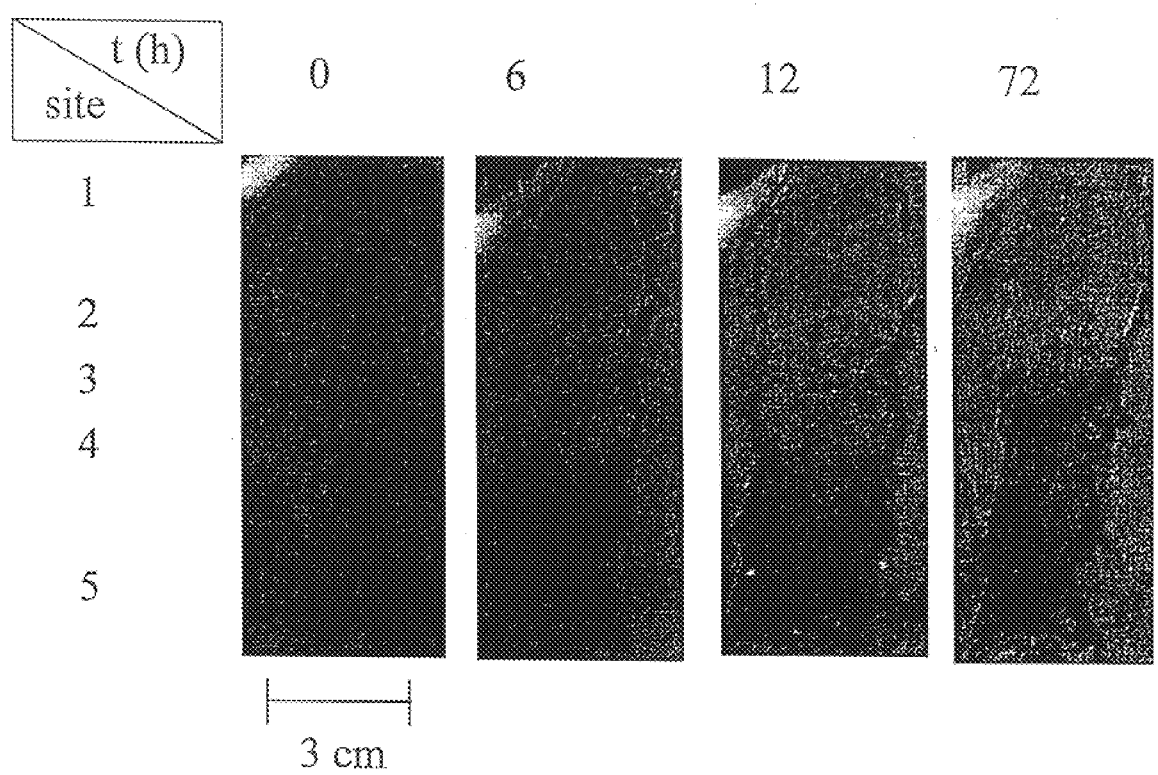
FIG. 3 is a sequence of images of the reverse McFarlane dorsal skin flap site taken immediately prior to surgery (t=0) and at 6, 12 and 72 hours post-elevation.
Figure 9:
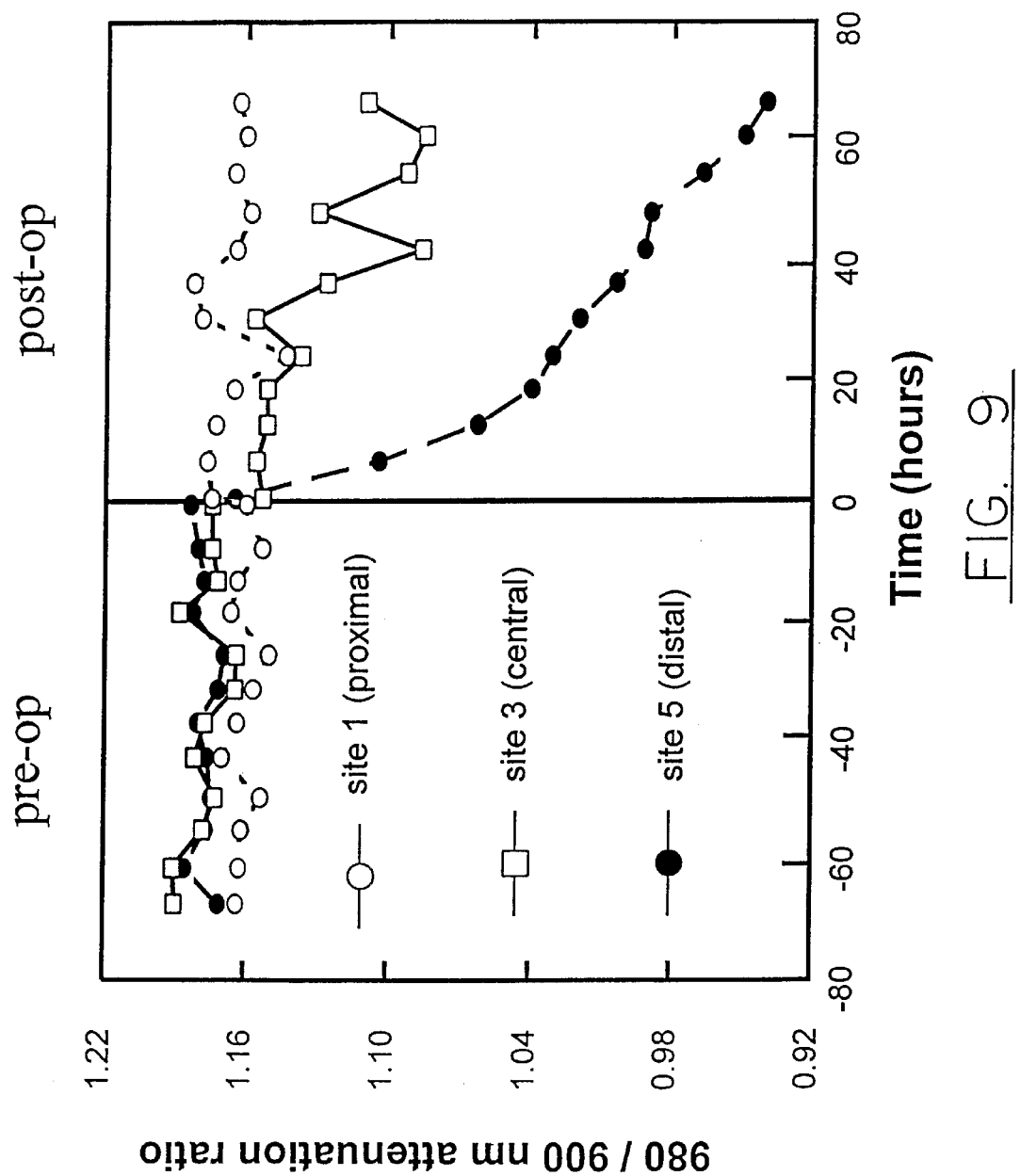

FIG. 9 is a comparison of the 72 hour pre-operative and post-elevation time courses of the tissue hydration index (980/900 nm attenuation ratio) proximal to the vascular pedicle (site 1) at the transitional central site (site 3) and the site distal to the pedicle (site 5) of the dorsal skin flap pictured in FIG. 3.

Figure 10:
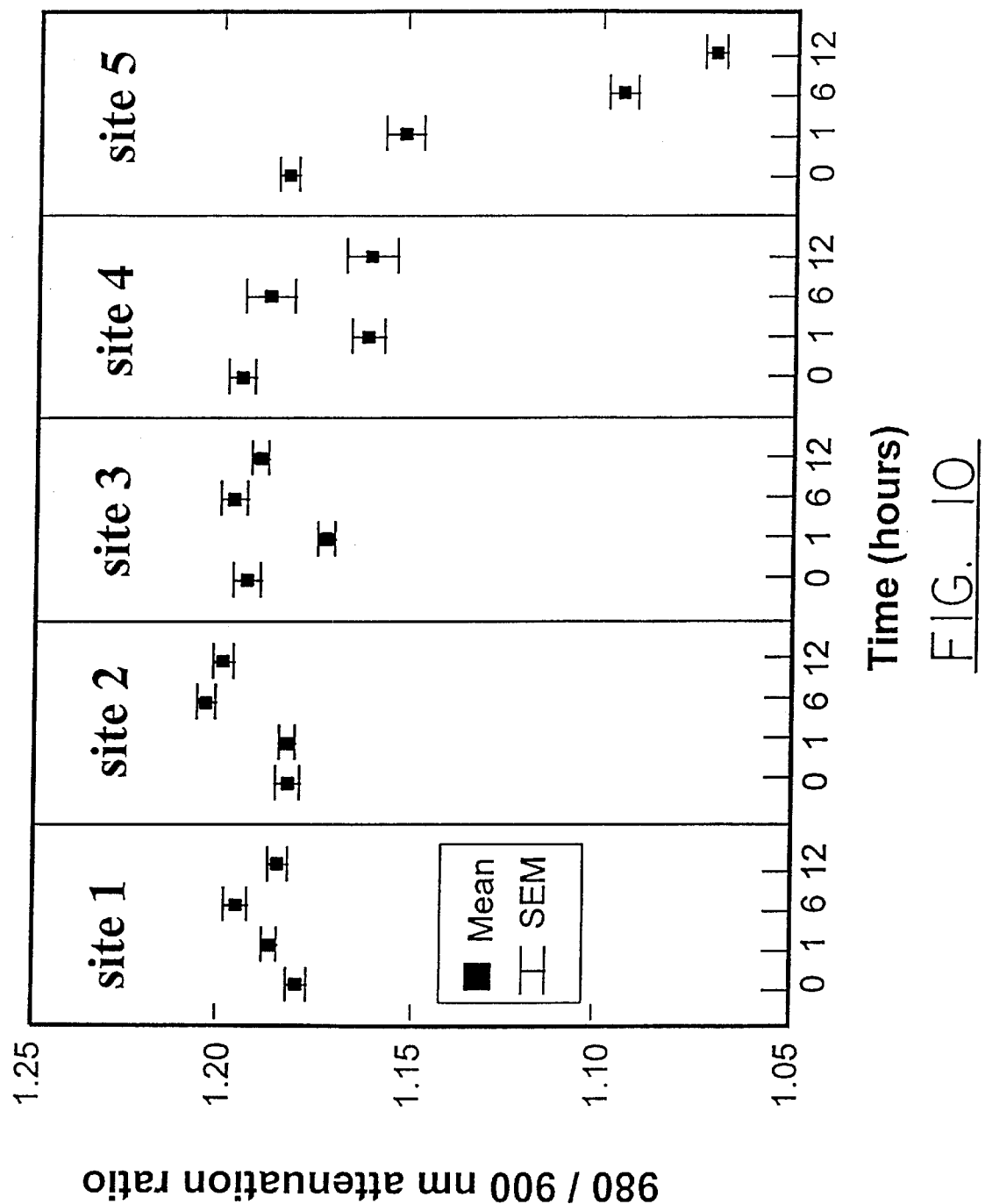

FIG. 10 is a comparison between the mean (SEM) tissue hydration index (980/900 nm attenuation ratio) at five selected sites along the reverse McFarlane dorsal skin flap (n=9) immediately prior to surgery (t=0) and within 1, 6 and 12 hours post-elevation of the flap.

Figure 11:
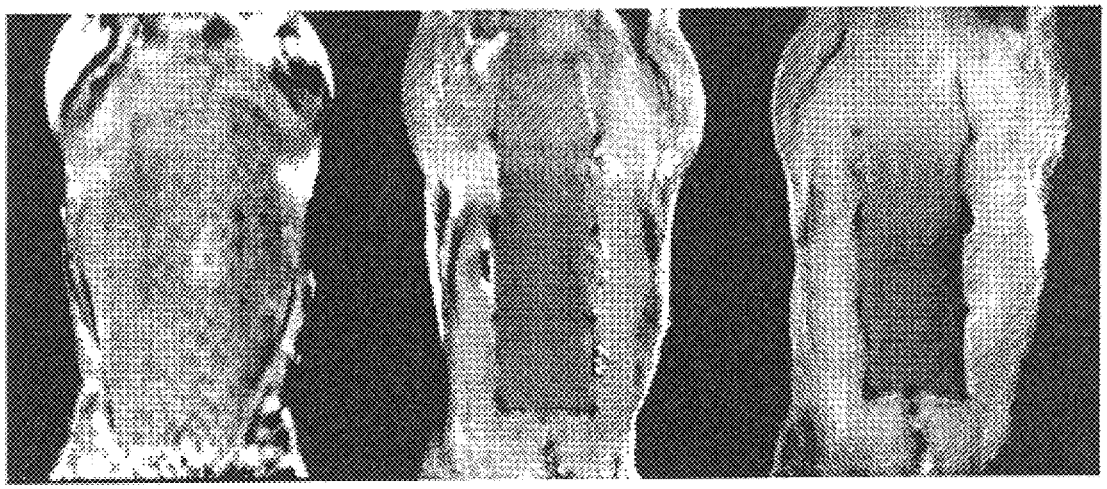

FIG. 11 is oxygen saturation images of a rat dorsum prior to surgery (left), 1 hour after surgical elevation of the reversed McFarlane skin flap (middle) and 6 hours following surgery (right).

Figure 12:
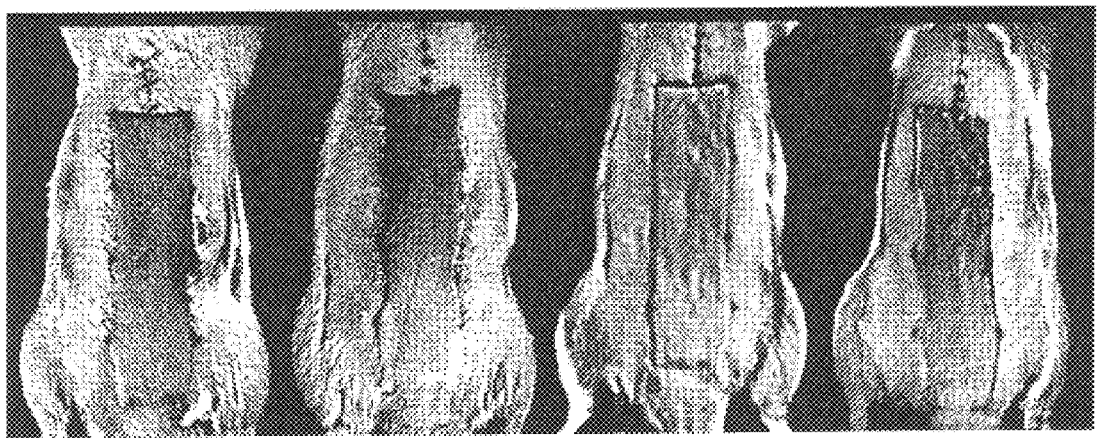

FIG. 12 is rat dorsal oxygen saturation images of reversed McFarlane skin flaps in four different animals taken 1 hour after surgical elevation of the flap.

Figure 13:
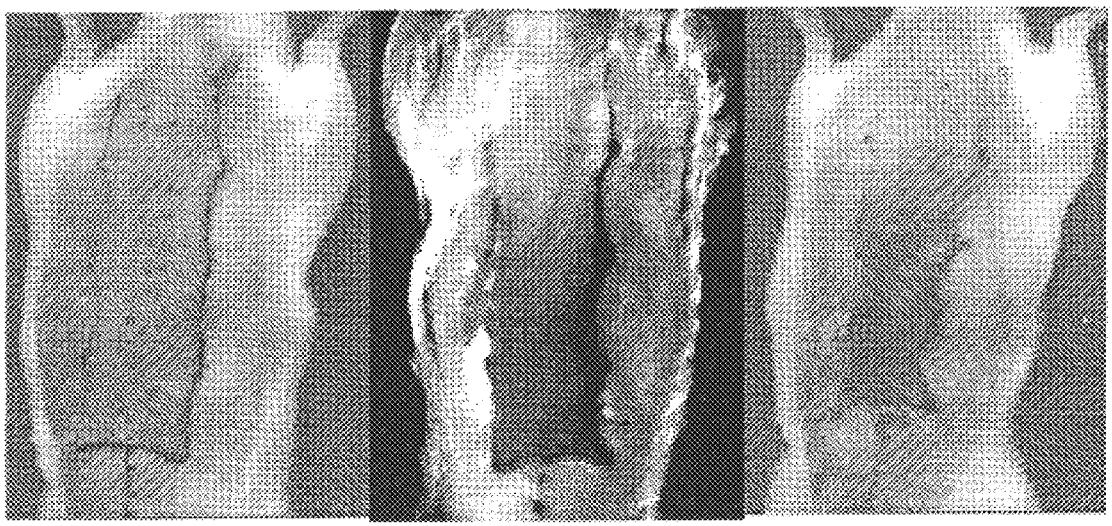

FIG. 13 is gray-scale visual image (left) and oxygen saturation image (middle) of rat dorsal reversed McFarlane skin flap 1 hour after surgery and gray-scale visual image (right) of the same rat dorsal flap 72 hours after surgery.

Figure 14:
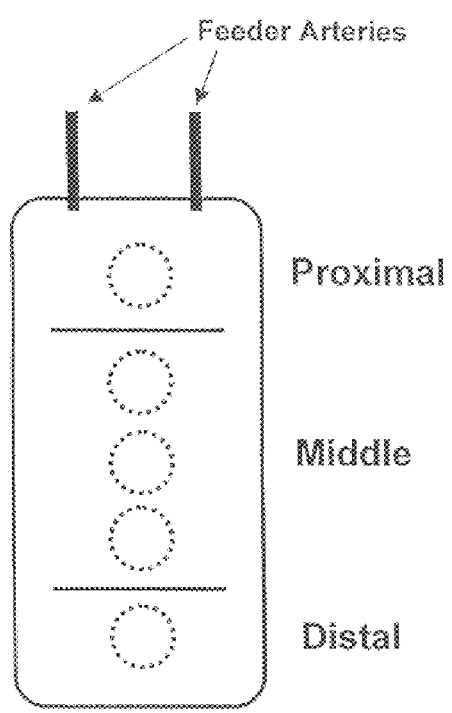

FIG. 14 is a schematic of the reverse McFarlane dorsal skin flap model indicating the two feeder arteries and the places where dashed circles were drawn using indelible ink.

Figure 15:
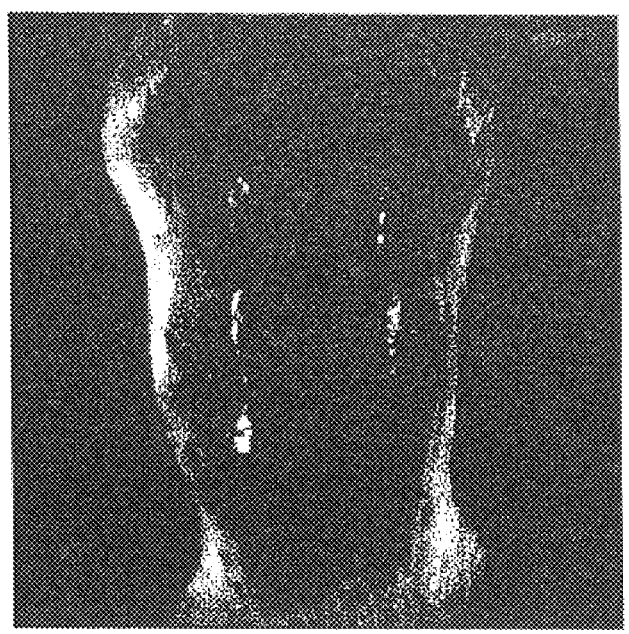

FIG. 15 is a 565 nm reflectance image of the rat dorsum immediately post-surgery.

Figure 16:
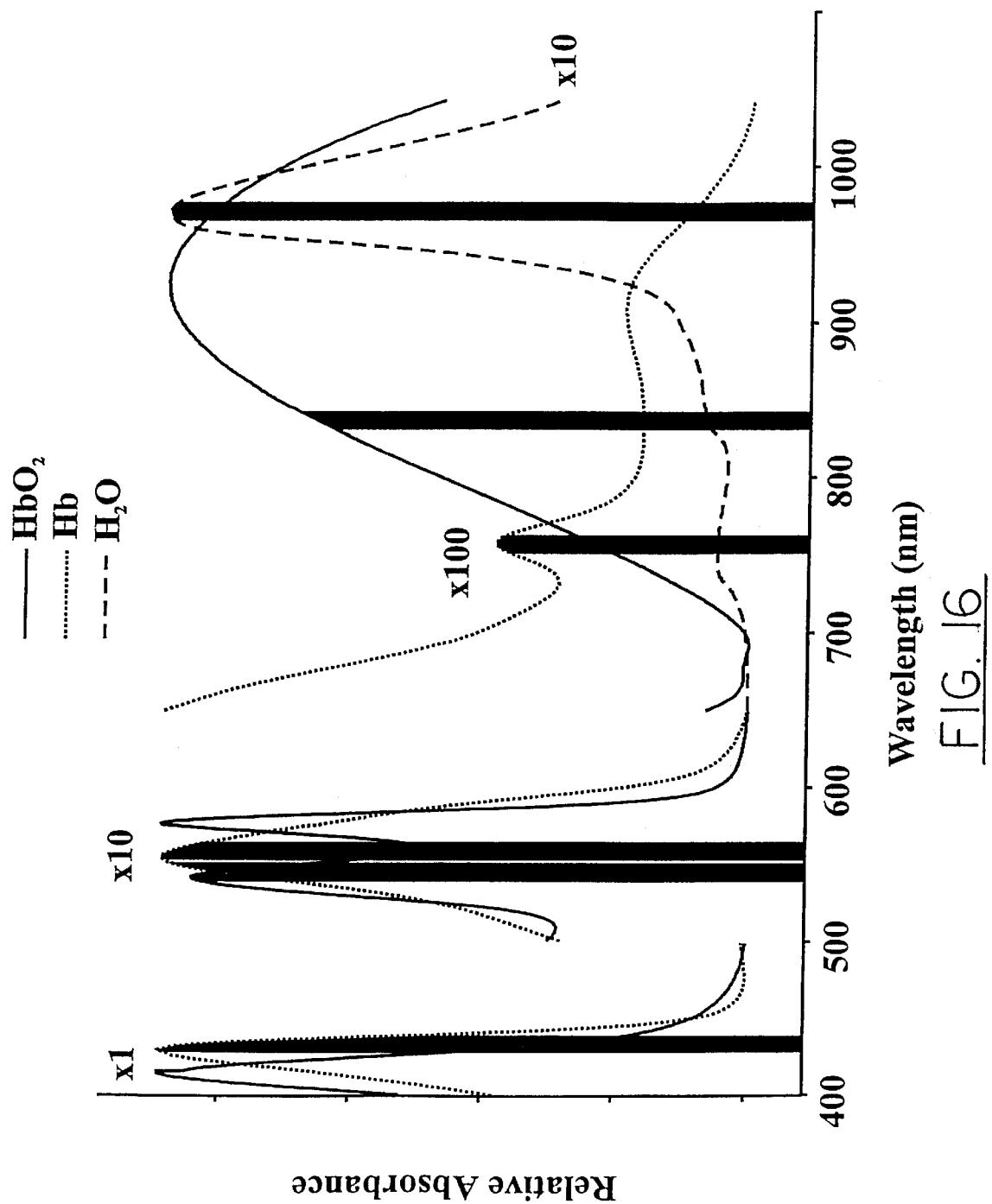

FIG. 16 is visible and near-IR spectra of oxygenated hemoglobin (solid line), deoxygenated hemoglobin (dotted line) and water (dashed line) with the wavelength regions covered by the bandpass filters superimposed thereon.

Figure 17:
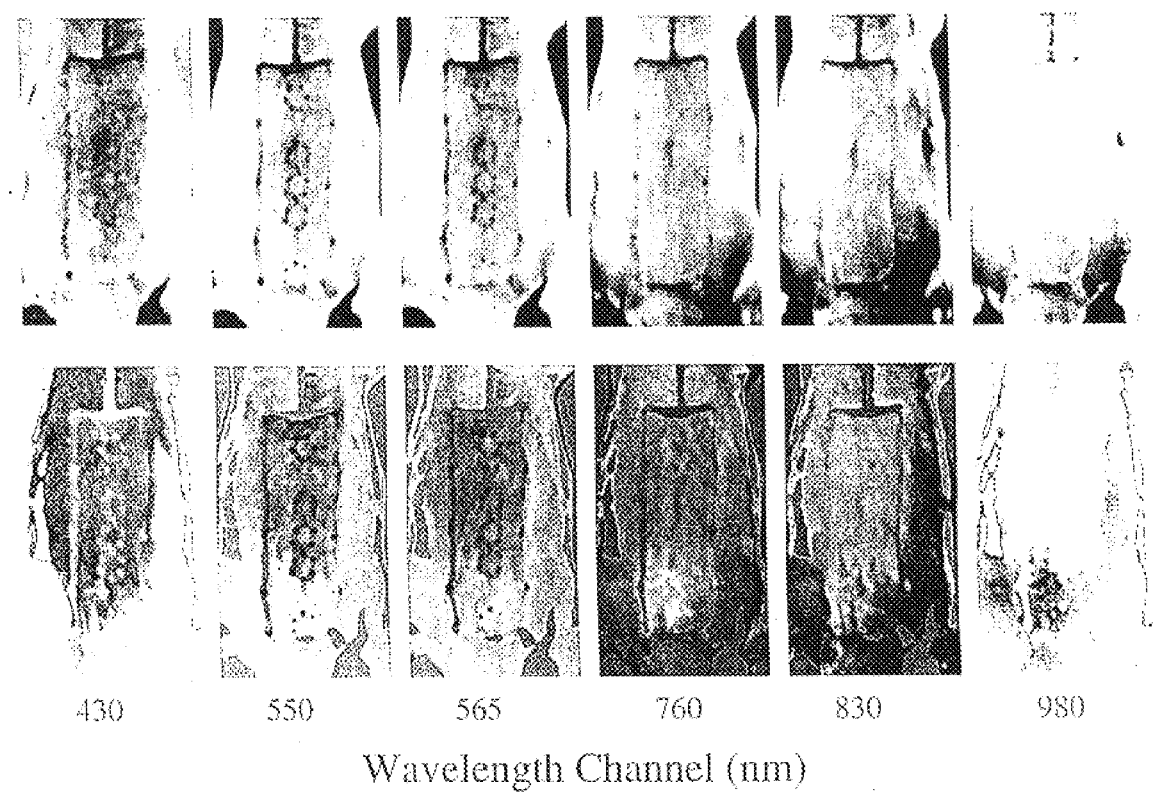

FIG. 17 is a pictoral depiction of raw (radiance) images obtained at 430, 550, 565, 760, 830 and 980 nm from the rat dorsal skin flap taken immediately following surgical elevation of the flap (upper panels) and corresponding statistically scaled, logarithmic residual corrected reflectance images (lower panels).

Figure 18:
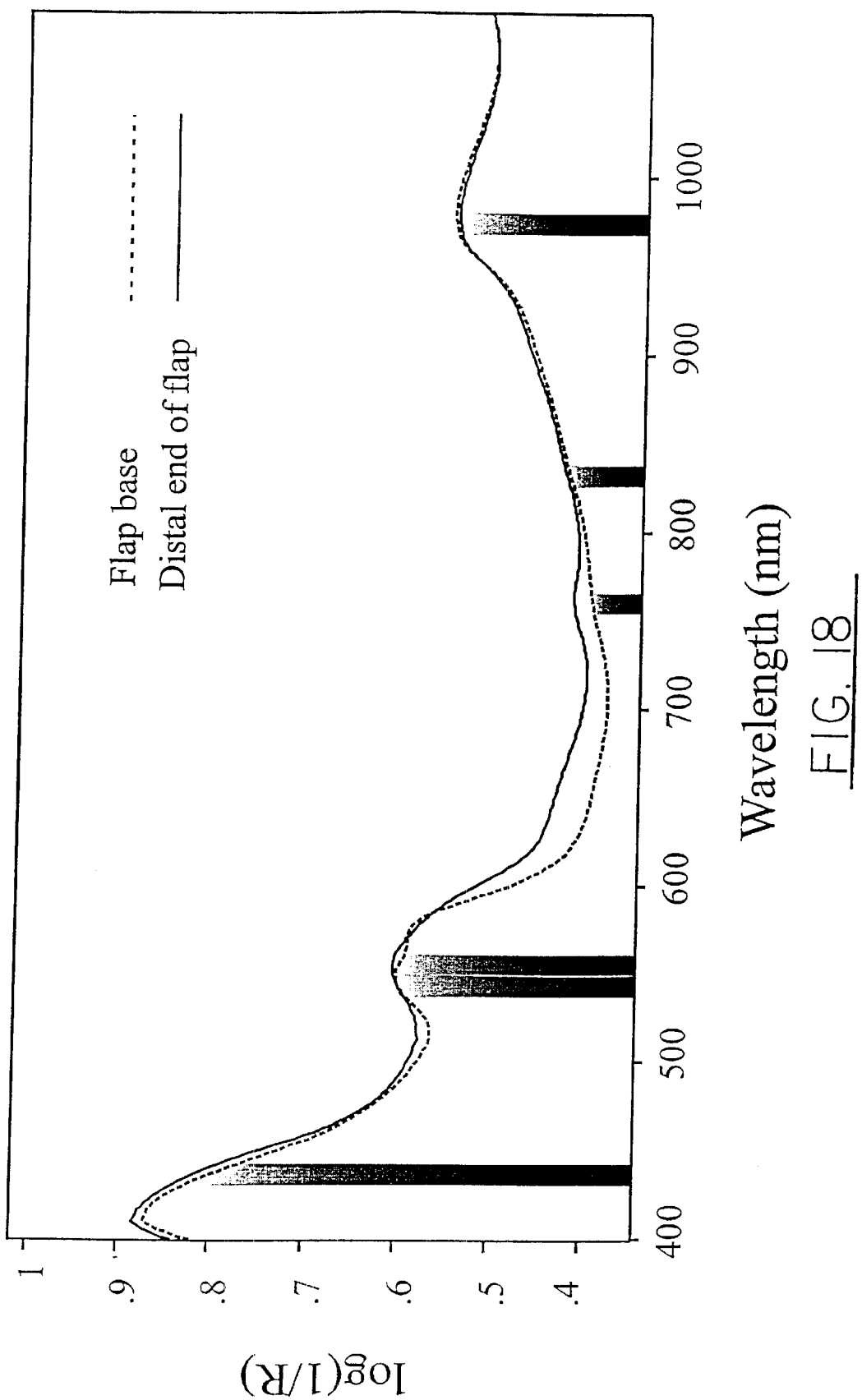

FIG. 18 is a radiance spectra of the rat dorsal skin flap taken immediately following surgical elevation of the flap from near the vascular base of the skin flap (dashed trace) and from near the distal end of the skin flap (solid trace) with the imaging wavelength channels shown as shaded bars.

Figure 19:
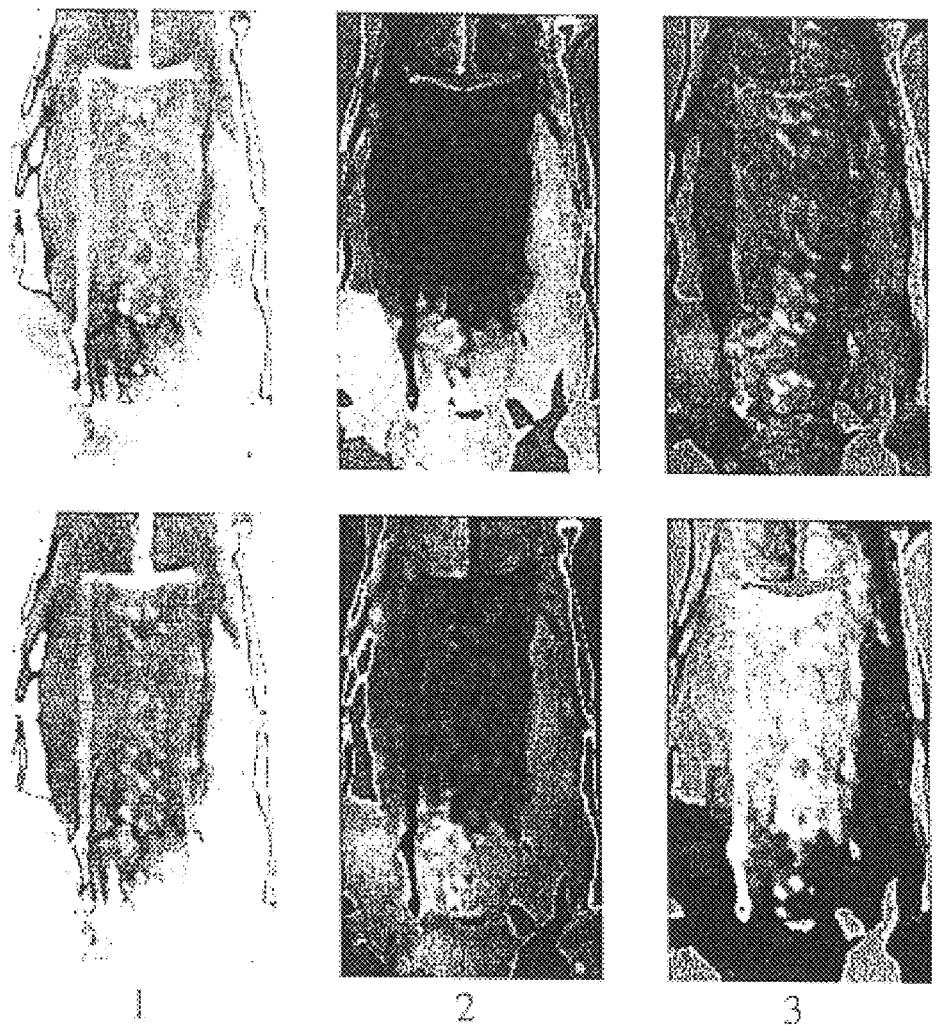

FIG. 19 is an illustration of the first three mean principal components (score) images based on the wavelength loadings in Table 4a (upper panels) and mean varimax rotated factor images based on the wavelength loadings in Table 4b (lower panels).

Figure 20:
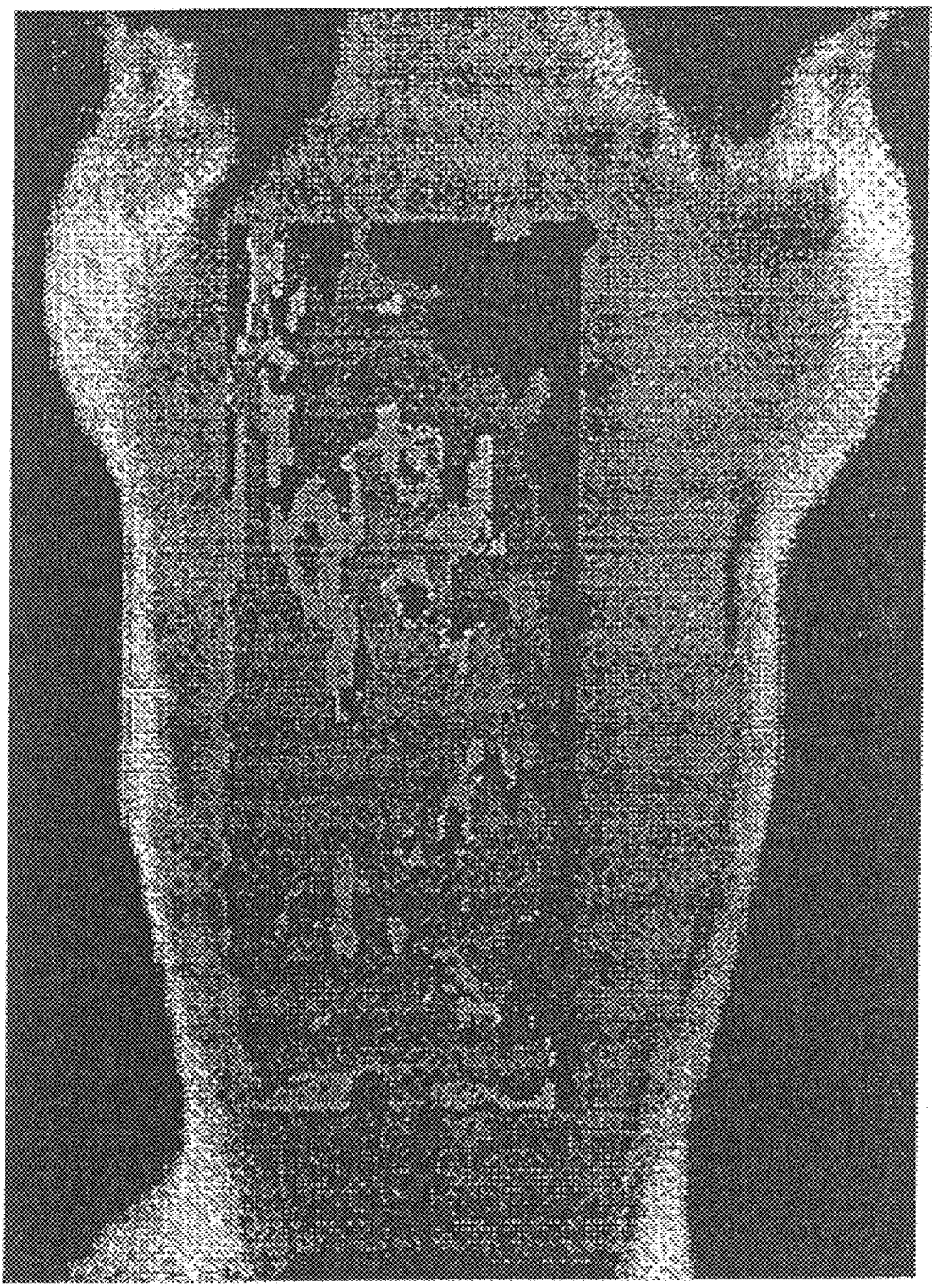

FIG. 20 is flap clustering results using statistical ISO-DATA clustering algorithm.

Figure 21:
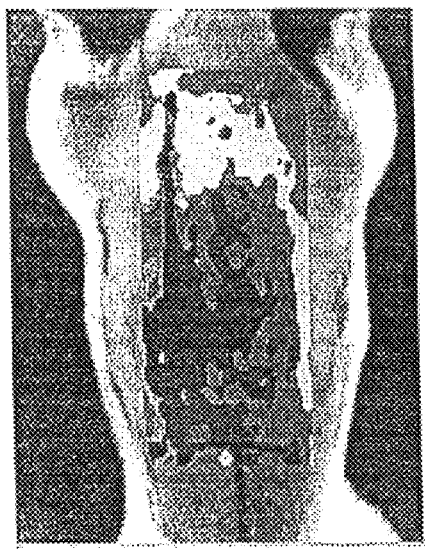
Figure 21:
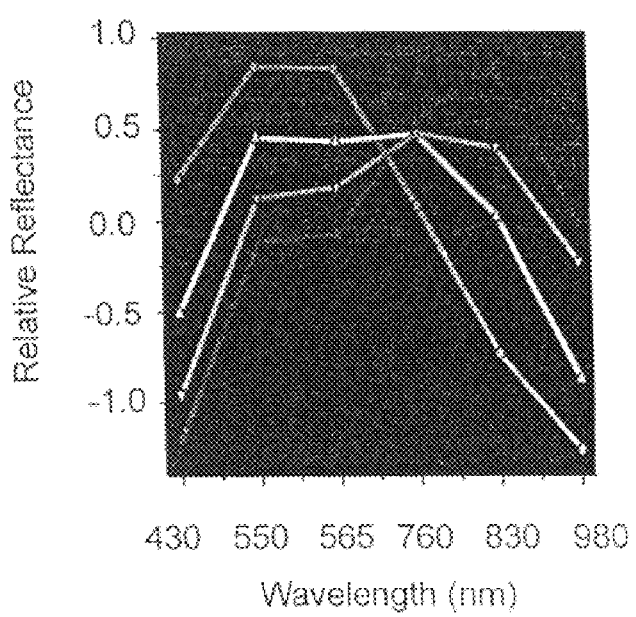

FIG. 21 is a four-cluster FCA membership map (left) and the corresponding cluster centroids (right).

Figure 22:
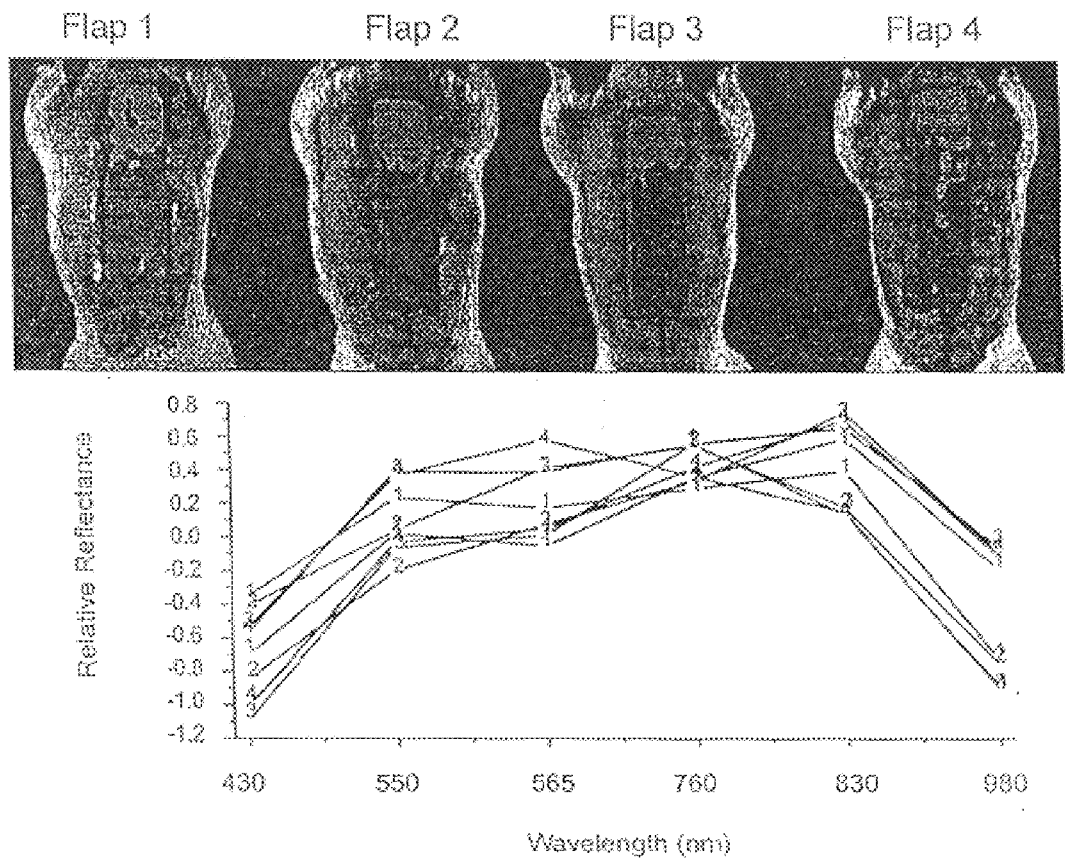

FIG. 22 is results of clustering the spectra pooled from four flaps into two clusters membership map (upper panel) and cluster centroids (lower panel), where the colour of the trace denotes to which cluster the spectrum belongs, and the numbers used as symbols for each data point denotes from which flap the centroid was derived.

Figure 23:
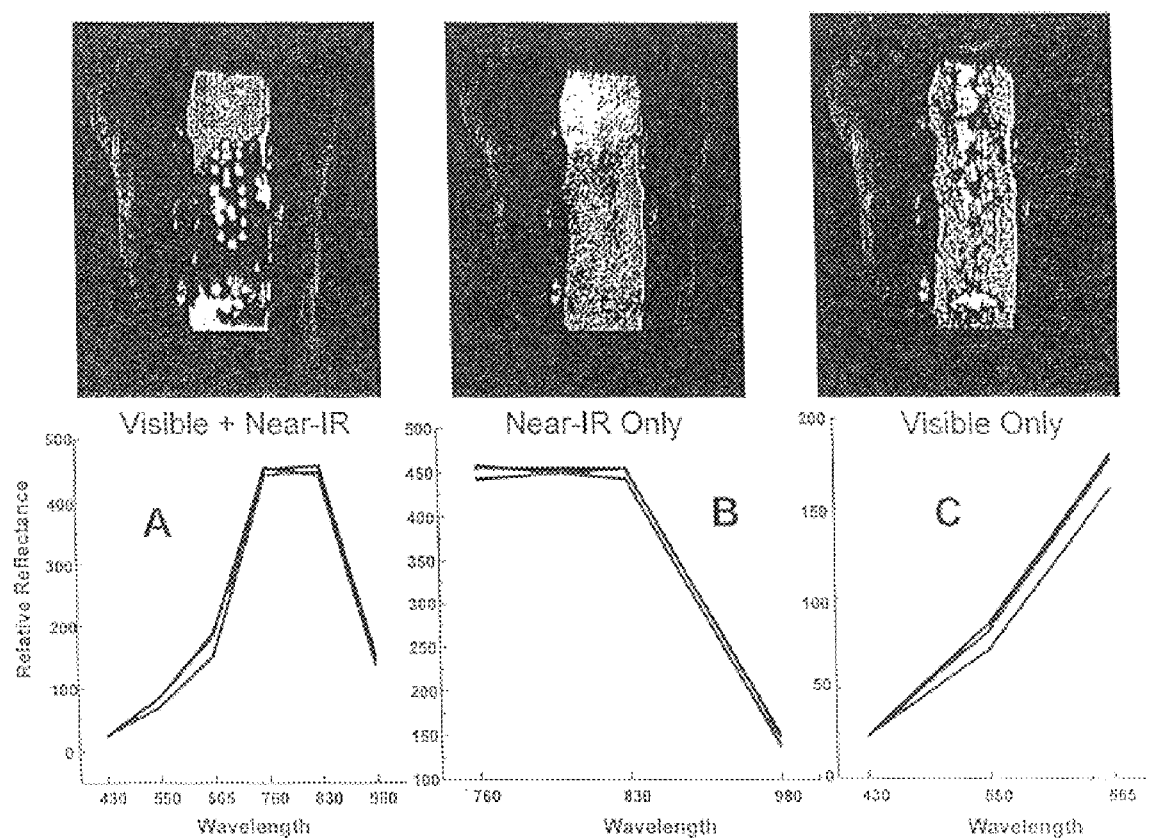

FIG. 23 is clustering results from the flap of rat 1 using various wavelengths: FIG. 23A shows the results using both visible and near-IR wavelength images, FIG. 23B displays the results of clustering analysis using only the near-IR wavelengths and FIG. 23C shows the results of the clustering analysis using only visible wavelengths.

Figure 24:
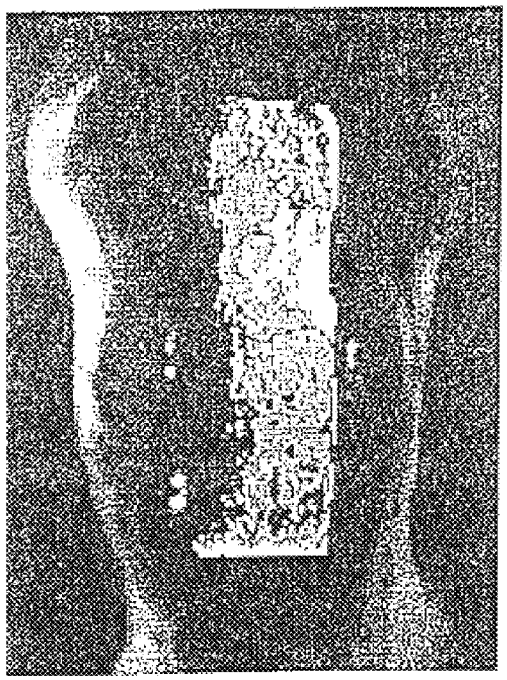
Figure 24:
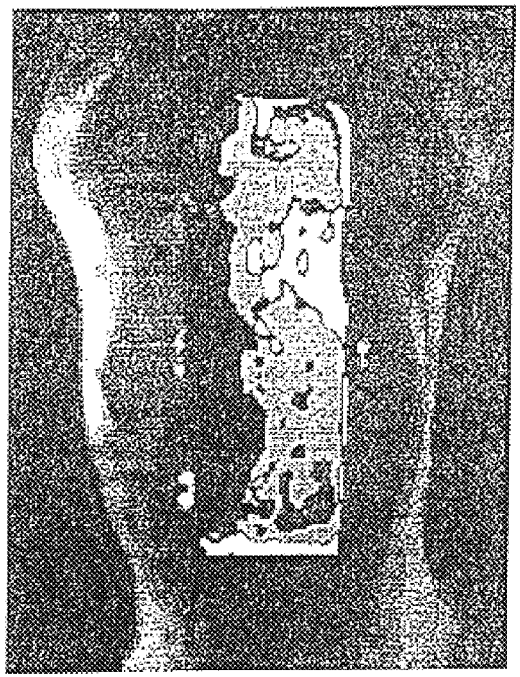
Figure 24:
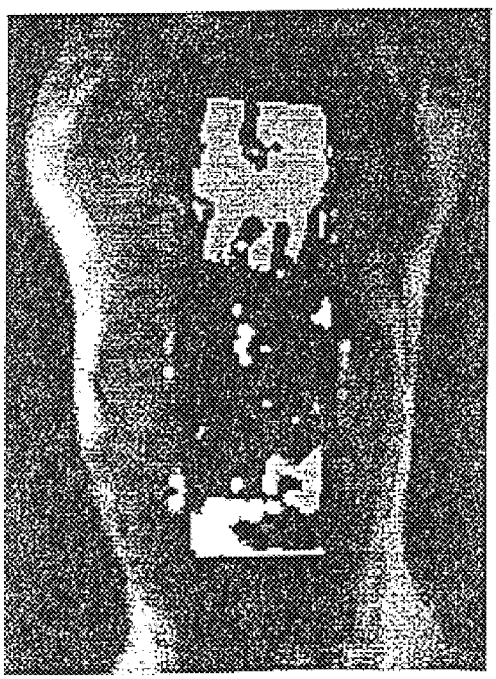
Figure 24:
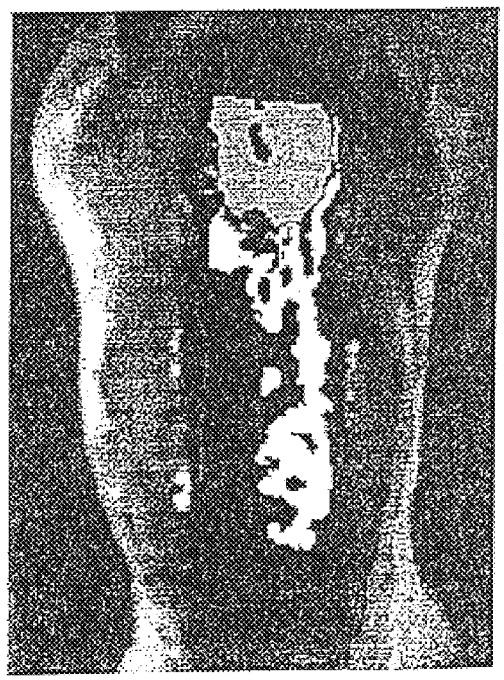

FIG. 24 is clustering the spectra of the flap of rat 1 into three clusters: FIG. 24A shows the results from the raw image data, FIG. 24B shows the results from the median filtered data, FIG. 24C shows the results from the log residual data and FIG. 24D shows the results from the statistically scaled data sets.

Figure 25:
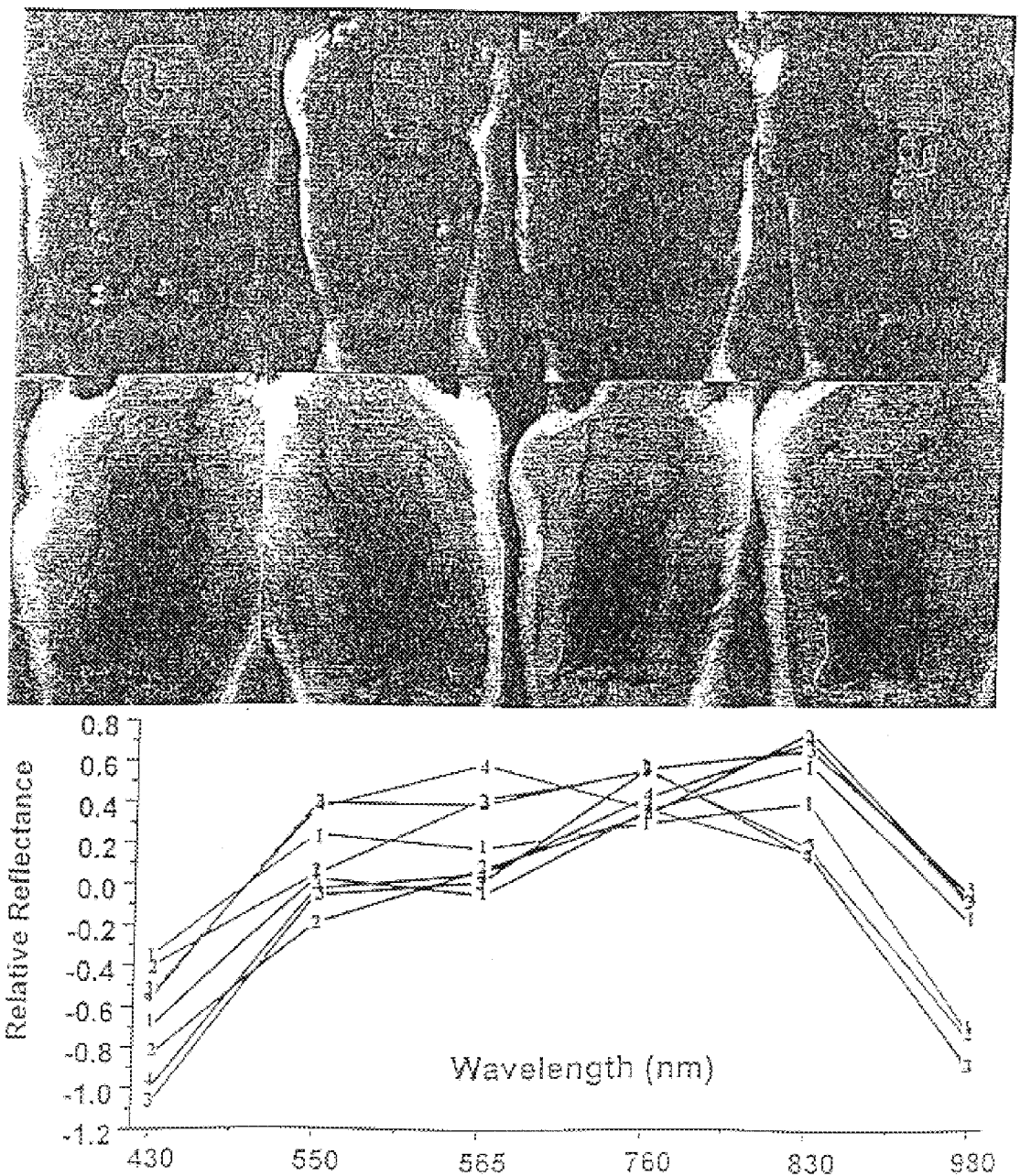

FIG. 25 is results from clustering the spectra from the log residual images taken 1 hour post-surgery (32081 spectra) of the flaps pooled from the four rats (FIGS. 25A to 25D, respectively) into two clusters; upper panel shows the clustering results superimposed on anatomical images, the middle panel shows colour images of the flaps taken at 72 hours post-surgery, and the lower panel shows the centroid spectra from the clusters of each of the flaps, where the color of the spectral trace denotes to which cluster the spectrum belongs and the number representing each data point denotes the flap from which the spectrum came.

Table 1 is mean (SD) hemoglobin oxygen saturation index, pooled pre-elevation measurements, immediately pre-elevation (t=0) and at 1, 6 and 12 hours post flap elevation.

Table 2 is mean (SD) tissue hydration index, pooled pre-evaluation measurements, immediately pre-elevation (t=0) and at 1, 6 and 12 hours post flap elevation.

Table 3 is Spearman ranked correlation coefficients between the wavelength channels of the multispectral radiance image averaged over the four reversed McFarlane skin flaps used, wherein bracketed figures represent the standard deviation in the calculated correlation coefficient over the four skin flaps.

Table 4a is percent variance accounted for the principal components of the multispectral reflectance image and the corresponding wavelength loadings for each of the principal components. Table 4b is the average wavelength loadings of the varimax rotated factors derived from the first 3 principal components of the multispectral reflectance image.

DETAILED DESCRIPTION

Herein, visible and near-infrared spectroscopy are used to analyze tissue hydration and oxygenation immediately following surgery. The data were acquired simply, rapidly and non-invasively. Furthermore, the data from a single spectrum is sufficient, using the method herein described, to predict tissue viability, obviating the need to continuously monitor trends. The measurements are consistent and reproducible with minimal inter- or intra-observer variation, and the collection of data does not pose any hazard to the tissue being studied. This is of paramount importance, as early, non-subjective detection of poor tissue oxygenation following surgery increases the likelihood that intervention aimed at saving the tissue will be successful and thus lead to improved clinical outcome in both skin flaps and grafts.

EXAMPLE I

Principles of Optical Near-infrared Tissue Spectroscopy

Infrared spectroscopy deals with the interaction of IR radiation with matter. The IR region of the electromagnetic spectrum is generally considered to lie in the wavelength range from 700–250,000 nm and is further subdivided into three subregions: The near-IR region, (from 700–2500 nm), the mid-IR region (from 2500–50000 nm) and the far-IR region (beyond 50000 nm). Visible and near-IR spectra in the 600 to 1100 nm range are presented in this study. The spectroscopy of tissues involves measuring the attenuation of the light intensity by the tissue relative to the incident light intensity.

Figure 1:
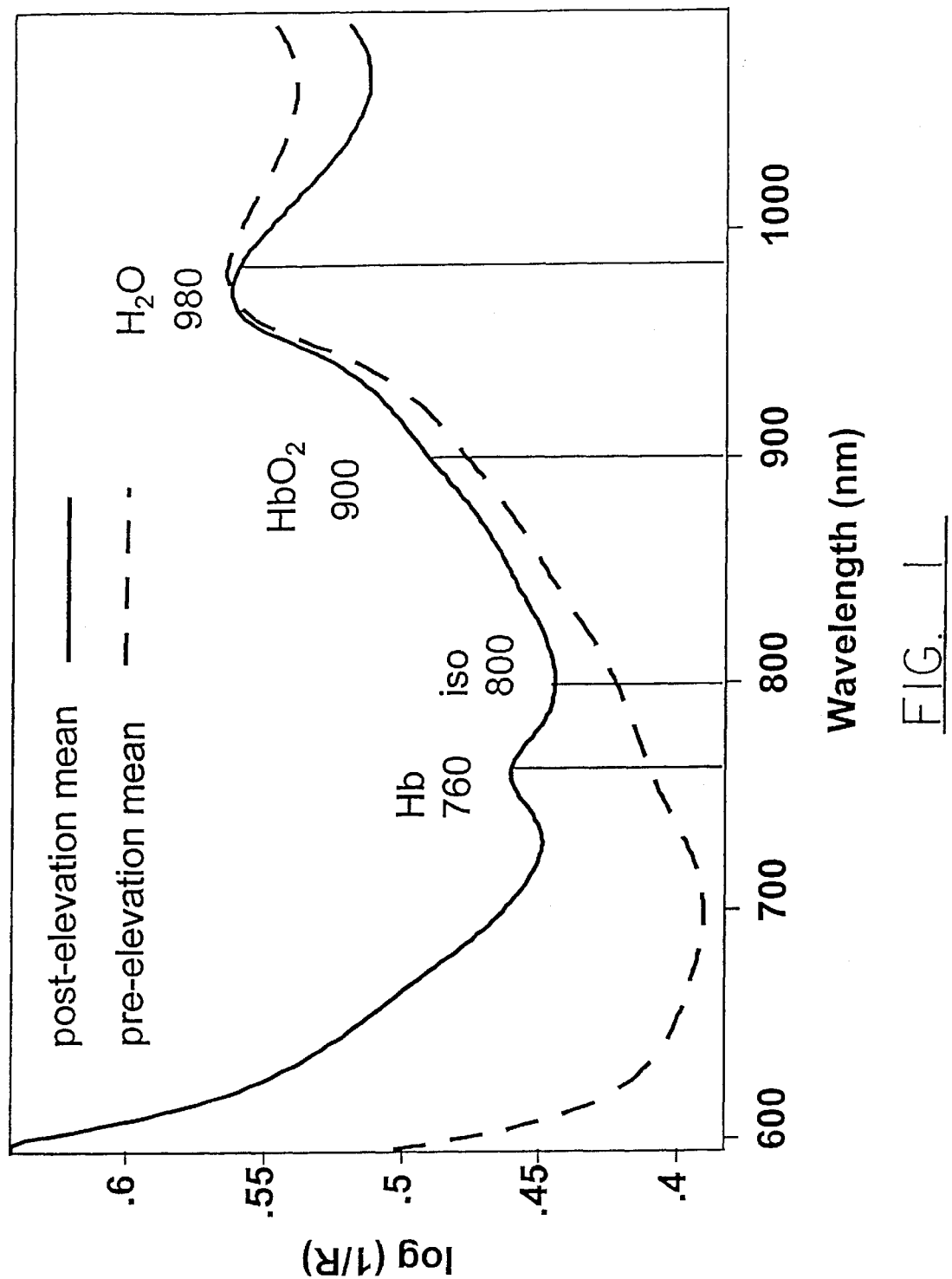
FIG. 1 is a mean near-IR spectra (600–100 nm) from the central site (site 3) of the flap pictured in FIG. 3.

Herein, the relative change and distribution of the levels of oxyhemoglobin (HbO$_2$), and deoxyhemoglobin (Hb) in tissue, following flap elevation is examined and these data are used to predict tissue viability. The near-IR and visible absorption spectra of Hb, HbO$_2$ and water are well understood and the differential absorption by these chromophores can be distinguished at certain characteristic wavelength regions (Eaton and Hofrichter, 1981, *Meth Enz* 76:175–261). As shown in FIG. 1, deoxyhemoglobin displays a small but distinct absorption maximum at 760 nm while oxyhemoglobin displays a much smaller relative absorption at that wavelength. The situation is reversed at 900 nm where HbO$_2$ displays a maximal absorption relative to Hb. The absorption coefficient of the two species is equal (an isobestic point) at 800 nm. A simple measure of the relative concentration of Hb independent of changes in tissue scatter and blood volume can be obtained by taking the ratio of the light attenuation at the nearby wavelengths of 760 and 800 nm. The 800/760 nm attenuation ratio provides a measure proportional to the hemoglobin oxygen saturation. In conventional oximetry, the 660/1900 nm light attenuation ratio is related to the percent oxygen saturation. However, due to interfering absorptions in the 660 nm region arising from other metabolites, the 660 nm band was not used in the measurement of hemoglobin oxygen saturation in our studies.

The seven wavelength channels selected for the multi-spectral images closely correspond to absorption band maxima or isobestic points for Hb, HbO$_2$ or H$_2$O (Cordone et al, 1986, *Biophys Chem* 24:259–275; Eaton and Hofrichter, 1981). The 760 nm channel closely corresponds to the charge transfer absorption band maxima of Hb, while the 800 nm channel is centred on the Hb/HbO$_2$ isobestic point which, as noted above, is where Hb and HbO$_2$ absorb equally. The 980 nm channel lies on the absorption maximum of H$_2$O and was not used in the oxygen saturation calculations. Variation in tissue blood volume results in a corresponding variation in the tissue reflectance at the wavelengths where Hb, HbO$_2$ and H$_2$O have a significant absorption. Spatial variation in hemoglobin oxygen saturation results in a change in the differential reflectance at absorption wavelengths associated with HbO$_2$ relative to wavelengths where Hb preferentially absorbs. However, reflectance intensity at isobestic wavelengths are unaffected by varying oxygen saturation. Reflectances changes which are observed at wavelengths where Hb and HbO$_2$ have a significant differential absorption but which do not correlate with reflectance changes at the Hb/HbO$_2$ isobestic reflectance wavelength arise from changes in tissue hemoglobin oxygenation changes which are independent of blood volume changes and changes in tissue scatter. Images based on the selected wavelengths can thus provide a measure of the blood volume or total hemoglobin (tHb), and the fraction of oxygenated hemoglobin (O$_2$sat).

Relative changes in hemoglobin (Hb) and oxyhemoglobin (HbO$_2$) concentrations were determined by fitting the absorption coefficients of the hemoglobins to the observed changes in the reflectance attenuation ($\Delta$OD) at several wavelengths (Matcher et al, 1995, *Anal Biochem* 227:54–68; Gagnon et al, 1996, *Eur J Appl Physiol* 73:443). The Moore-Penrose generalized inverse (Eubank and Webster, 1985, *Amer Stat* 39:64–66) of the rectangular absorption coefficient matrix was used to obtain the least squares estimate of the relative change in hemoglobin (Hb) and oxyhemoglobin (HbO$_2$) concentration.

$$\begin{bmatrix} \Delta[\text{Hb}] \\ \Delta[\text{HbO}_2] \end{bmatrix} = pinv \begin{bmatrix} a_{700}^{\text{Hb}} & a_{760}^{\text{Hb}} & a_{850}^{\text{Hb}} & a_{900}^{\text{Hb}} \\ a_{700}^{\text{HbO}_2} & a_{760}^{\text{HbO}_2} & a_{850}^{\text{HbO}_2} & a_{900}^{\text{HbO}_2} \end{bmatrix} \begin{bmatrix} \Delta OD_{700} \\ \Delta OD_{760} \\ \Delta OD_{850} \\ \Delta OD_{900} \end{bmatrix}$$

Hemoglobin oxygen saturation (O$_2$sat), which corresponds to the fraction of oxygenated hemoglobin, was derived from predicted Hb and HbO$_2$ concentration changes.

$$\Delta\ O_2\text{sat} = \Delta \left[ \frac{\text{HbO}_2}{\text{HbO}_2 + \text{Hb}} \right]$$

Two or more wavelengths centred about the isobestic point were used for both the broadband near-IR spectroscopic evaluation of oxygen saturation as well as for the calculation of oxygen saturation images. Optical density changes were taken relative to the optical density at the isobestic point, OD$_{800}$, in order to provide oxygen saturation values independent of blood volume changes and changes in tissue scattering.

All calculations were performing using the Interactive Data Language (IDL, Research Systems Inc., Boulder, Colo.) on a Silicon Graphics Challenge series server (SGI, Mountain View, Calif.).

I. Near-IR Spectroscopy

EXAMPLE II

Anaesthesia and Surgical Procedures

3×10 cm reverse McFarlane flaps raised on the dorsa of 9 Sprague Dawley rats weighing between 380–410 grams were used. The rats were acclimatized for a minimum period of 2 weeks prior, and the individual surgeries were performed over a three month period. All the procedures were done under 1.2–2% isoflurane inhalational anaesthesia. Five days prior to surgery, rats were shaved and a depilatory agent (Nair™) was applied on the rat dorsum. At that time, reproducible anatomic points for the near-IR spectroscopy measurements were marked on the skin, as shown in FIG. 2.

Surgery was performed 3 days (72 h) after pre-elevation measurements, which were to be used as control values in the analyses. Prior to surgery, the flap location was defined and marked based on the location of the sacral vessels, following which pre-elevation images and spectra were acquired. Twenty minutes prior to surgery, the rats were premedicated with 0.05 mg/kg of atropine sulphate administered sub-cutaneously in the ventral abdomen. The rats were then anaesthetized and placed on a circulating water blanket in order to maintain body temperature at 37° C. during surgery. Body temperature was monitored throughout surgery using a rectal temperature probe. The surgery was done under aseptic conditions. A 3 cm wide and 10 cm long flap was raised consisting of skin and underlying panniculus carnosus based on the sacral vessels. A triangular piece of skin and panniculus carnosus was taken as a free graft from the dorsum of the rat just beyond the flap. The flap donor site was then sutured in a straight line, starting at the point of the triangular defect. The graft was inset along the dorsum adjacent to the base of the flap. The flap was then stretched to its 10×3 cm dimensions and was sutured over the skin of the back. Antibiotic ointment (furacin) was applied around the flap edges. At the end of the surgical procedure, a cervical collar was placed around the neck of each rat such that it did not interfere with the animal's feeding or watering habits, but prevented injury to the surgical site and the flap. Post-operative analgesia was provided using Buprenorphine 25 μg/kg (administered sub-cutaneously) every 12 h for the remaining duration of the experiment.

During the three-day (72 h) post-operative observation period, the animals were housed separately. Post-operatively, near-IR measurements were carried out within 1 h of flap elevation and then every 6 h. FIG. 2 illustrates the dorsal reversed McFarlane skin flap model used in the present study. In this model, the flap derives its blood supply from two sacral vessels at the base of the flap. The base of the flap, proximal to the blood supply, is expected to be well perfused while the distal end of the flap is poorly perfused. Blood flowing to the distal end of the flap should also be poorly oxygenated. Thus, parameters related to hemoglobin oxygen saturation are expected to vary along the length of the flap. After a 72 h post-operative observation period, a final visual assessment of the flap was made, after which the rat was sacrificed.

EXAMPLE III

Near-infrared Measurements

Near infrared radiance images of 256×256 pixels were collected at 650, 700, 760, 800, 850, 900 and 980 nm using a Photometrics Series 200 CCD camera fitted with a Nikon Macro AF60 lens using 10 nm bandpass (FWHH) Lyot type filters (OCLI, Santa Rosa, Calif.). Visible and near-IR spectra were collected with a NIRSystems 6500 (Perstop, Silver Springs, Mass.) spectrometer using a custom bifurcated fiber optic bundle (CeramOptic, Enfield, Conn.). A 99% Spectralon® reflectance standard (LabSphere Inc.) was used as a reference to convert raw data into reflectance spectra. Each reflectance spectrum consisted of 32 co-added scans collected between 600–1100 nm at 10 nm resolution.

Pilot studies indicated that approximately the distal half of the flap failed while the half proximal to the vascular pedicle remained viable. Five dorsal monitoring sites were located along the length of the flap, as shown in FIG. 2. In order to have reproducible anatomical points for the near-IR measurements, five sites were marked on the dorsum using a 3×10 cm silastic template which had five circular zones cut-out. The diameter of the circles (1 cm) was equivalent to the diameter of the fiber optic probe used for the spectroscopic measurements. Two measurement sites were located on the proximal half of the flap and two sites on the distal half of the flap. The central measurement site typically spanned the transitional area between the viable and necrotic sections of the flap.

Three near-IR measurements were performed at every dorsal monitoring site for each time point in the monitoring sequence. These sites were monitored every 6 h for a total of 72 h prior to surgical elevation of the flap and for a further 72 h at 6 h intervals immediately following the elevation of the flap. A total of 24 monitoring time points were acquired over the complete monitoring sequence. Along with the near-IR measurements, a corresponding colour digital image of the rat's dorsum was taken at each time point in the monitoring sequence. This enabled an accurate correlation between the clinical picture and the near-IR spectra. The total time to carry out a full assessment in all zones averaged 17 min.

EXAMPLE IV

Statistical Analysis

All near-IR attenuation ratios are tabulated as means of the three measurements taken at each assessment. Analysis of variance (ANOVA) using three factors, number of animals (N=9), measurement site (1–5) and time after flap elevation (0, 1, 6 and 12 h, respectively) was used to evaluate the results. Post-hoc comparison of means was carried out using the Tukey HSD multiple comparison test (STATISTICA, StatSoft, Okla.). Differences were considered significant at $p<0.01$.

EXAMPLE V

Results

Figure 4:
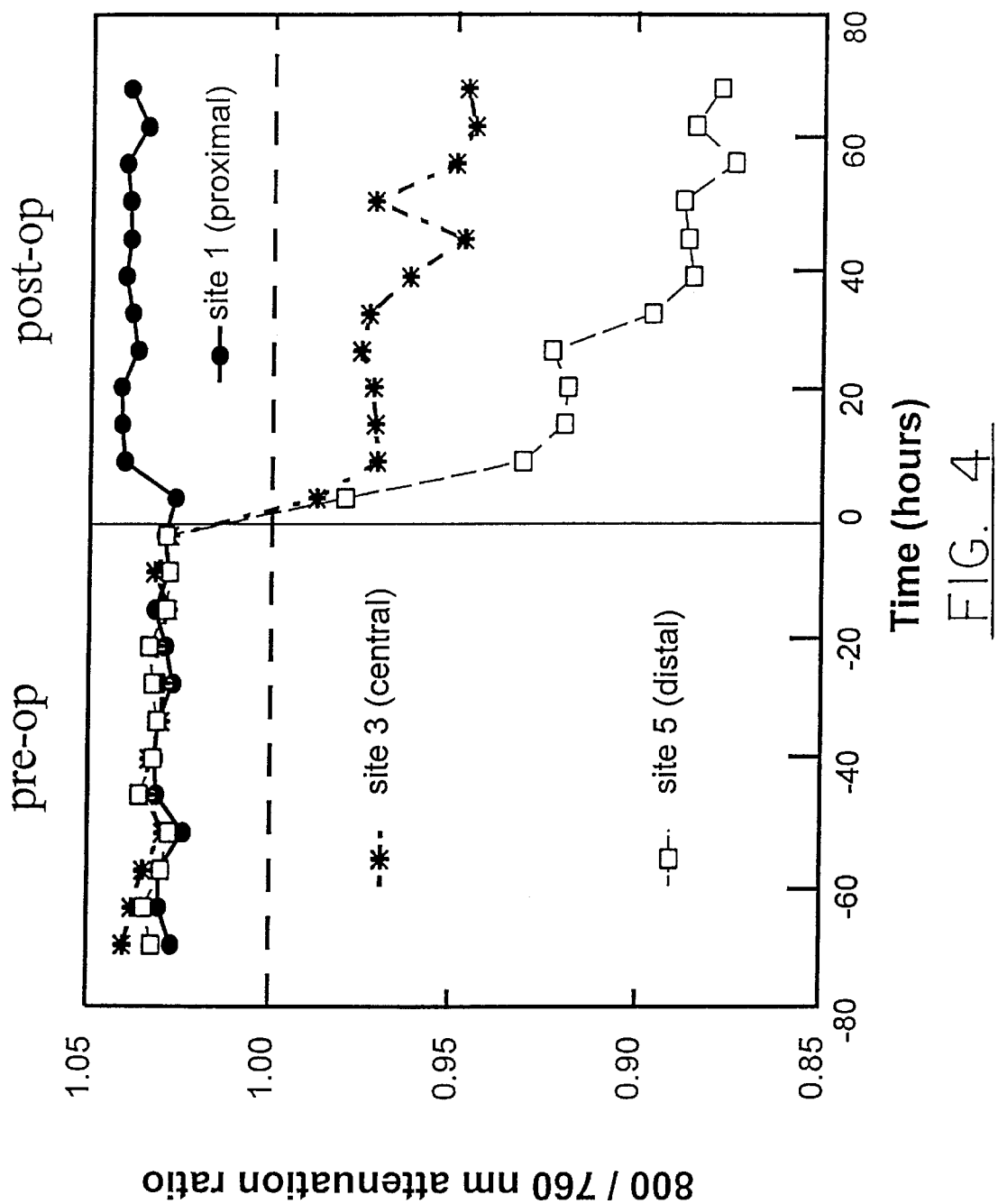
FIG. 4 is a comparison of the 72 hour post-operative and post-elevation time courses of the hemoglobin oxygen saturation index (8001760 attenuation ratio) proximal to the vascular pedicle (site 1), at the transitional central site (site 3) and the site distal to the pedicle (site 5) of the reverse McFarlane dorsal skin flap depicted in FIG. 3.

All animals tolerated surgery, repeated anaesthesia and measurements without visible adverse systemic effects. FIG. 3 presents a sequence of colour images taken of a shaved rat dorsum which shows the spectroscopic measurement sites and anatomical landmarks prior to raising the flap (0) as well as 6, 12 and 72 h after elevation. A representative comparison of the mean near-IR spectrum acquired at the central measurement site (site 3) over the pre-(dashed trace) and post-(solid trace) elevation 72 h observation period is shown in FIG. 4.

Figure 5:
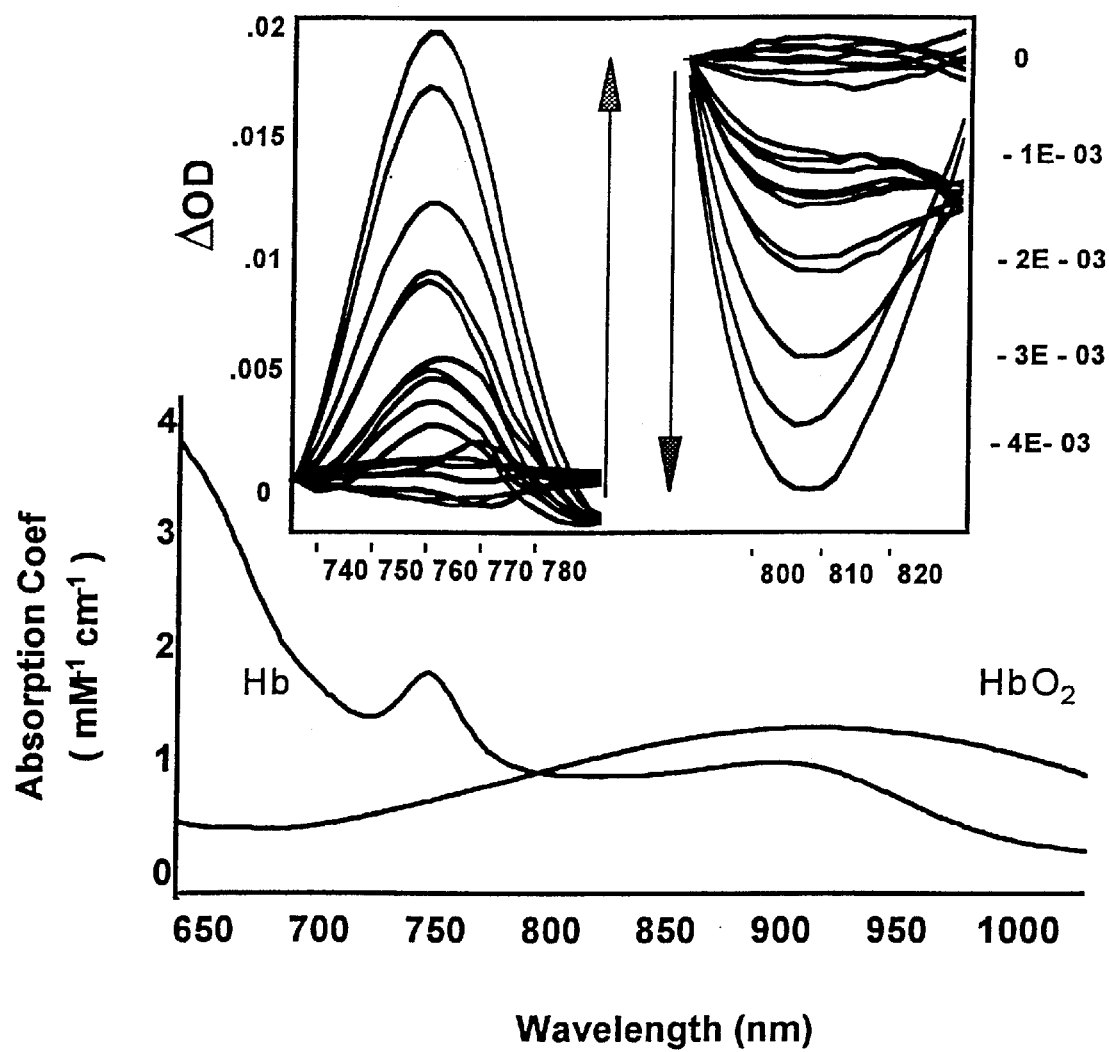
FIG. 5, upper panel is a graph of optical density changes relative to $Hb/HbO_2$ isobestic point following surgical elevation of the reversed McFarlane skin flap; lower panel is a graph of absorption coefficients in the spectral region 650–1080 nm of hemoglobin (Hb), oxyhemoglobin ($HbO_2$).
Figure 6:
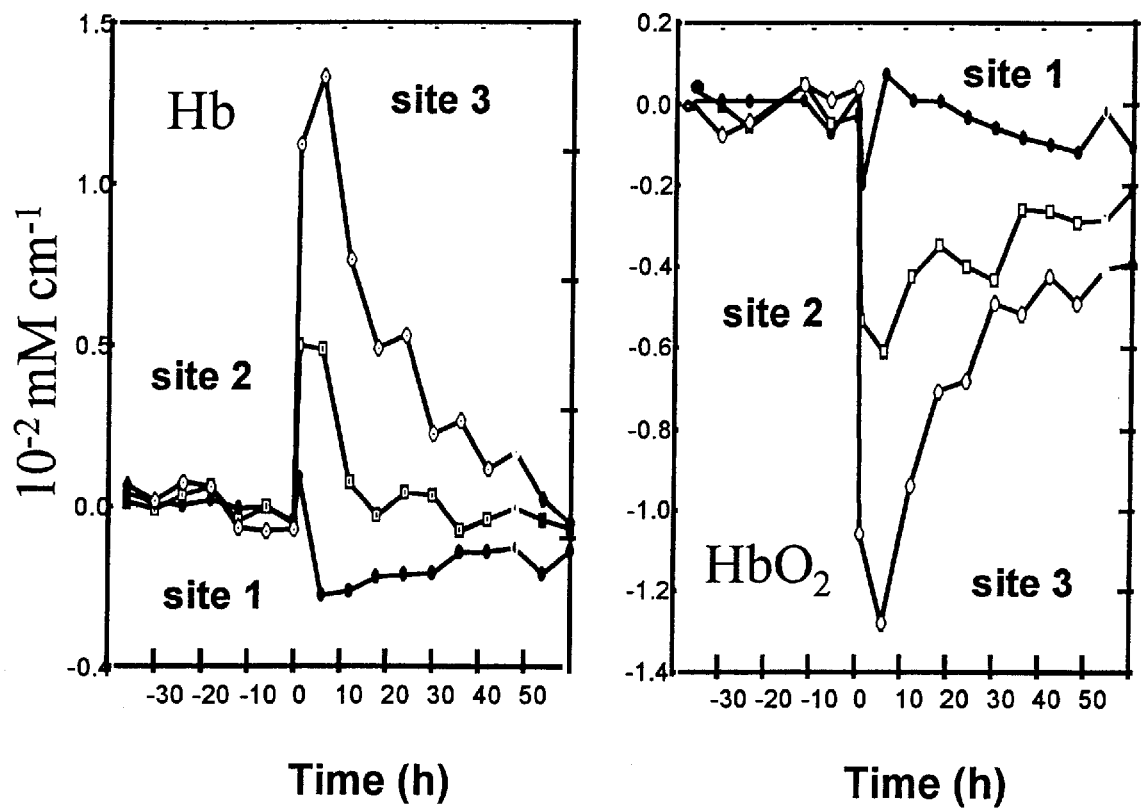
FIG. 6 is a graph of changes in Hb and $HbO_2$ concentration per unit photon pathlength at measurement sites 1–3 of the reversed McFarlane skin flap over a 30 hour pre-operative monitoring period (indicated by negative times) and a 50 hour post-operative monitoring period (indicated by positive times).

FIG. 5 shows the optical density changes following surgical elevation of the flap relative to the optical density at the $Hb/HbO_2$ isobestic point. At wavelengths shorter than the 800 nm isobestic point, the optical density increases upon surgical elevation of the skin flap while at the longer wavelength side of the isobestic point, there is a corresponding decrease in optical density. This negatively correlated behavior between the optical densities at the shorter and longer wavelength sides of the isobestic point are indicative of tissue oxygen saturation changes following surgical elevation of the skin flap. The absorption coefficients of Hb and $HbO_2$ presented in FIG. 1 highlight the differential absorption characteristics of Hb and $HbO_2$ in the region of the 800 nm isobestic point. Utilizing the absorption coefficients for Hb and $HbO_2$ at the shorter and longer wavelength side of the isobestic point and the relative change in optical densities at those wavelengths, the relative changes in Hb and $HbO_2$ concentration (per unit photon pathlength) can be determined. FIG. 6 traces the relative change in Hb and $HbO_2$ concentration at the measurement sites 1–3 in a flap for 30 h prior to surgery and a 50 h post-operative time period.

The Hb and $HbO_2$ concentration shows little variation over the 30 h pre-operative monitoring period. In addition, there is no significant difference in the relative Hb and $HbO_2$ concentrations between flap measurement sites 1–3. Immediately following surgical elevation of the flap, sites 1–3 display a significant increase in the relative Hb concentration, which is mirrored by a corresponding drop in the $HbO_2$ concentration. Measurement site 1, which is closest to the base of the flap and hence closest to the blood supply, shows a rapid recovery with relative $HbO_2$ concentrations exceeding pre-operative values at the 6 h post-operative monitoring time point. Site 3, which is further from the vascular base of the flap, shows an even more dramatic drop in the relative $HbO_2/Hb$ concentration following surgical elevation of the flap and a correspondingly slower and incomplete recovery over the intervening 50 h. The behavior in the $HbO_2/Hb$ concentration at measurement site 2 which lies between the sites 1 and 3, is intermediate to the $HbO_2/Hb$ concentration changes observed at the adjacent sites, 1 and 3.

EXAMPLE VI

Hemoglobin Oxygen Saturation

The ratio of the light attenuation at 800 and 760 nm provides a measure proportional to the hemoglobin oxygen saturation. This saturation index is largely independent of tissue blood volume changes, or changes in tissue scattering, since changes in these parameters affect the 760 and 800 nm wavelengths of light equally thus leaving the attenuation ratio unaffected.

FIG. 4 plots the 144 h time course of hemoglobin oxygen saturation measurements for the same flap whose visual image is shown in FIG. 3. Clinically, the most interesting time points occur in the first 12 h following the raising of the flap. Table 1 compares the mean (SD) of the 800/760 nm attenuation ratio (oxygen saturation index) taken at 5 separate monitoring sites along the shaved rat dorsum. The first column tabulates saturation values pooled over the 72 h pre-operative monitoring period for each site. Hemoglobin oxygen saturation measurements taken immediately prior to elevating the flap, t=0 h, and at 1, 6 and 12 h after flap elevation at each flap site are tabulated in columns 2–5 respectively of Table 1. FIG. 8 compares the pooled means (standard error of measurement [SEM]) of the oxygen saturation index (800/760 nm attenuation ratio) of the oxygen saturation index for sites 1–5 over the first 12 h following flap elevation.

Broad-band near-IR spectroscopic results indicate that tissue oxygenation can be determined based on the relative optical density changes at two or more wavelengths on either side of the $HbO_2/Hb$ isobestic point. FIG. 8 reports an index which correlates with tissue oxygen saturation utilizing just two wavelengths: 760 and 810 nm. This index provides a highly reproducible measure of tissue oxygenation status.

The results pooled over all animals (N=9) show the same general trend in oxygenation as observed for the single flap presented in FIG. 5. Site 1 suffers from a small drop in oxygenation immediately following surgery but oxygenation is fully recovered by 6 h. Site 2 shows a more dramatic drop in oxygen saturation upon surgery that is fully recovered within 12 h of the surgery. The drop in oxygenation is roughly the same at sites 3–5 but more pronounced than that observed for site 2. The further the site is away from the vascular base of the flap, the more pronounced is the drop in oxygen saturation over the next 12 h. On average, sites 4 and 5 rapidly become necrotic within 36 and 12 h, respectively, while in the reversed McFarlane skin flap model, site 3 is at a transitional location. In approximately half the cases, site 3 should remain viable over the full 72 h time-course, while in the other half of the cases the site should become necrotic. In this particular study, site 3, on average, failed over the 72 h clinical observation period.

EXAMPLE VII

Tissue Hydration Index

The full 144 h time course of the hydration index is plotted in FIG. 9. This hydration index time course corresponds to the oxygen saturation index time course presented in FIG. 4 and the flap images depicted in FIG. 3. Comparisons of the mean (SD) of the 980/900 nm attenuation ratio (hydration index) taken at 5 separate monitoring sites is seen in Table 2. The first column of tabulated values are pooled over the 72 h preoperative monitoring period, while columns 2–5 report the hydration index at t=0, 1, 6 and 12 h respectively after elevating the flap. FIG. 10 reports the tissue hydration index for sites 1–5 at the time point immediately prior to surgery (t=0) and within 1, 6 and 12 h after elevating the flap.

Oxygen saturation images calculated from multi-wavelength near-IR spectroscopic images correlate with the broad-band spectroscopy findings. FIG. 11 compares a pre-operative oxygen saturation image (left image) to images collected 1 h (middle image) and 6 h (right image) following surgery. Dark regions in the oxygen saturation images correspond to regions of reduced oxygenation.

Prior to surgery, oxygenation over the entire shaved dorsum is relatively uniform. After surgical elevation, the entire flap appears darker than the surrounding uninvolved tissue. This indicates reduced oxygenation over the entire flap. These imaging results are consistent with the findings based on the broad-band spectroscopy results which indicate a sudden drop in oxygen saturation, even at the site closest to the blood supply upon surgical elevation of the skin flap. The 1 h oxygen saturation image also clearly reveals an oxygen saturation gradient along the length of the skin flap. At 6 h, the base of the flap (top of image), which is nearest the vascular blood supply, has fully recovered and has an oxygen saturation comparable to the uninvolved tissue surrounding the flap. Oxygen saturation at the distal portions of the flap (towards the bottom of the image) has deteriorated compared with the 1 h image. Again, these imaging results are consistent with the spectroscopic findings reported in FIG. 6.

FIG. 12 compares the oxygen saturation images taken 1 h following surgery of four reversed McFarlane skin flaps. Despite the large inter-animal variation in the magnitude of the response, a clear oxygen saturation gradient is apparent along the length of the flaps with the tissue furthermost from the vascular base of the flap (top of the image in this case) displaying a much larger drop in oxygen saturation compared with tissue close to the vascular base (bottom of image). In all cases, the oxygen saturation near the base is near that of the surrounding uninvolved tissue. The large inter-animal variation in the magnitude of the response has several potential sources including the health of the animal and quality of the surgical procedure. However, the single most important factor is likely to be the size and number of sacral vessels feeding the flap which was observed to vary considerably from animal to animal.

Oxygen saturation images collected within 1 h following surgery clearly distinguish poorly oxygenated regions of the flap from regions with normal tissue oxygenation. These regions can not be distinguished by conventional clinical assessment techniques before 6 h following surgery. Thus, oxygen saturation images provide the surgeon with almost immediate feedback as to the oxygenation status of the flap. In absence of further surgical or pharmacological intervention, regions of poor oxygenation will not survive. FIG. 13 compares a gray-scale visual picture of the flap at 1 h post-elevation (left image), with the 1 h oxygen saturation image (middle image) and the 72 h visual picture of the clinical outcome of the flap.

EXAMPLE VII

Pre-operative Variations in Hemoglobin Oxygen Saturation

Skin blood flow is known to vary between adjacent sites. Thus, superficial blood flow along the rat dorsum might be expected to be heterogeneous, changes are due to variations in vascular tone in both the micro- and macro-circulation. Measurements of the oxygen saturation index made on the intact dorsum prior to elevation are highly reproducible over the 72 h pre-operative monitoring period as well as being consistent between the 9 animals in the study population. The standard deviation of these measurements pooled over dorsal sites and animals was less than 1% of the mean. Despite the high reproducibility, further statistical analysis (ANOVA using two factors, animals N=9 and measurement sites 1–5) revealed statistically significant inter-animal and inter-site variability in the oxygen saturation index. The high reproducibility of the measurements is clearly advantageous for the development of a clinically reliable method. However, the statistically significant inter-animal and inter-site indices suggest that the methodology may have the sensitivity required to measure the small variations in tissue heterogeneity hemoglobin oxygen saturation across the rat dorsum and between the dorsa of different animals. This sensitivity may in fact complicate the development of a universal tissue viability index, applicable across a broad set of tissue types and patient population.

EXAMPLE IX

Hemoglobin Oxygen Saturation, Post-operative Comparisons

Figure 7:
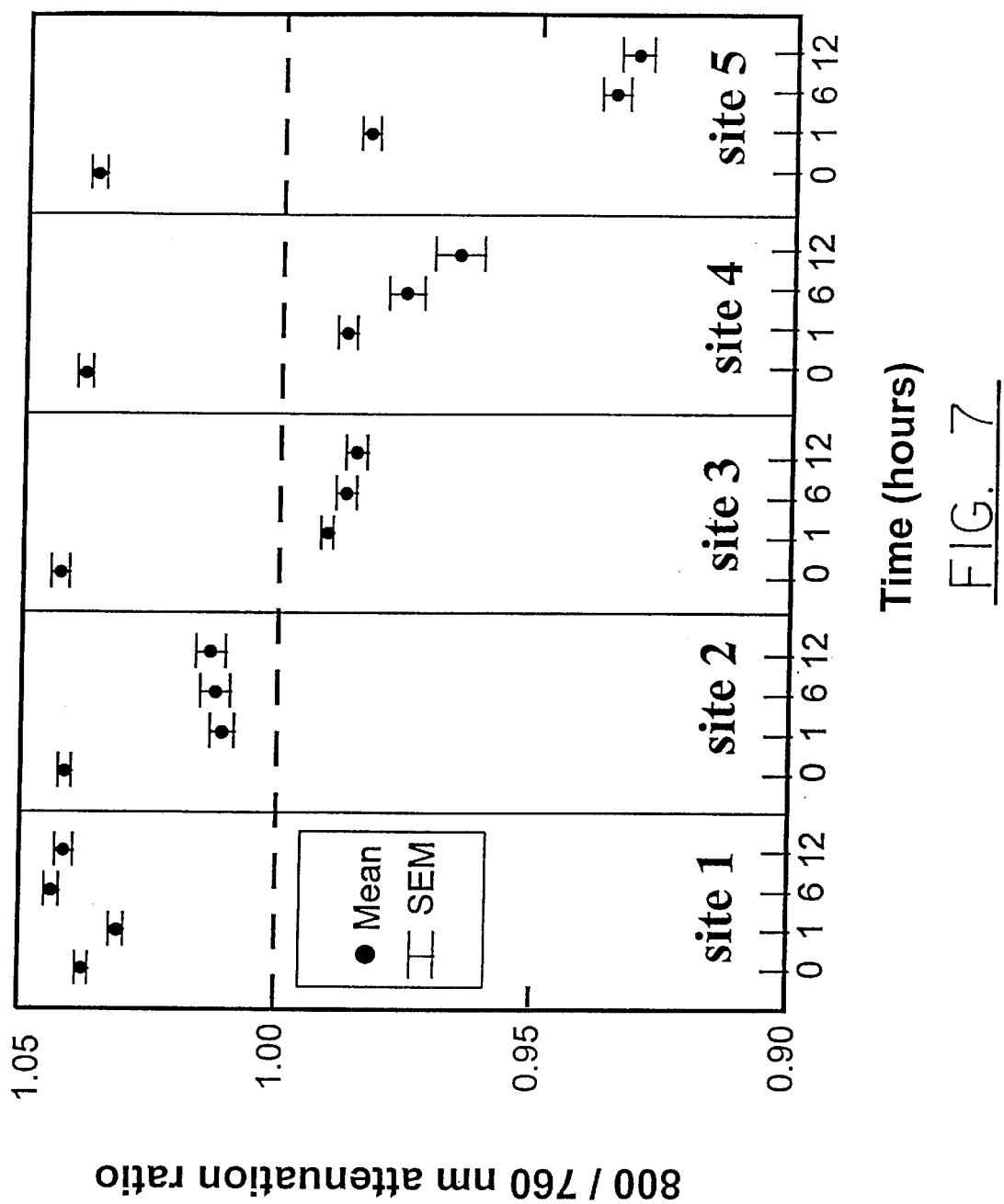
FIG. 7 is a comparison between the mean (standard error of measurement) hemoglobin oxygen saturation index (800/

The site most proximal to the vascular pedicle (site 1) is expected to be the least affected by raising the flap. As evident from the representative time course (FIG. 4) and the results pooled over the study population (FIG. 7), site 1 displays the least change in tissue hemoglobin oxygen saturation over the post-operative monitoring period. However, despite the small effect at the proximal site there were statistically significant differences between the oxygen saturation indices measured at different time points. Within an hour of elevating the flap, there is a small but significant ($p<0.01$) decrease in the oxygen saturation index at the proximal site (FIG. 7) which by 6 h recovered and is generally higher than its pre-operative value. There was no statistically significant differences in the oxygen saturation index between the 6 and 12 h measurements ($p=0.65$). These data suggest an initial decrease in the hemoglobin oxygen saturation at the base of the flap nearest the pedicle upon raising the flap which after 6 h recovers and exceeds that measured prior to raising the flap. Beyond 12 h, the hemoglobin oxygen saturation recovers to its pre-operative value and remains stable for the remainder of the 72 h monitoring period. In all the cases studied (N=9), this most proximal site remained viable over the 72 h post-operative monitoring period.

The more distal sites show a dramatic decrease in hemoglobin oxygen saturation upon raising the flap. The oxygen saturation index at the site next nearest to the pedicle (site 2), displays a much smaller initial decrease than sites further from the pedicle. In addition, at site 2, after the initial decrease, there was no significant difference between the mean saturation indices measured at 1, 6 and 12 h after elevating the flap. Typically the oxygen saturation index remained stable over the remainder of the experiment. In general, site 2 remains viable. However, our results indicate that the tissue at this site remains hypoxic for up to 72 h following flap elevation and the hemoglobin oxygen saturation does not recover to its pre-operative state.

At site 3 the mean oxygen saturation index decreased within 1 h of raising the flap and continued to decrease slowly over the first 12 h. The decrease was not statistically significant ($p>0.1$). When the oxygen saturation index at site 3 remained below 1 for the first 12 h after elevation, the site proceeded to fail over the next 60 h. However, in cases where the oxygen saturation index exceeded 1, site 3 remained viable for the duration of the experiment.

Measurement sites 4 and 5 were located at distal sites along the flap which typically failed within 72 h post-elevation. Within 1 h of elevation, the oxygen saturation index at these sites dropped by approximately the same magnitude as that observed for the central site (site 3). However, unlike the central transitional site (site 3) there was a further decrease in the oxygen saturation index within 6 h post-elevation ($p<0.01$). By 6 h a clear demarcation line can usually be observed extending across site 5 and to the edge of measurement site 4 (see FIG. 3). These observations correlate with the marked drop in hemoglobin oxygen saturation at sites 4 and 5 over the first 6 h following elevation. The magnitude of the drop in hemoglobin oxygen saturation between 1–6 h post-elevation correlates with the rate of necrosis. The drop in hemoglobin oxygen saturation between 1–6 h at site 4 is significantly less than that observed at site 5. Site 4 proceeds towards necrosis at a slower rate than site 5, generally becoming visibly necrotic within 24 h post-elevation.

These hemoglobin oxygen saturation results suggest that rat dorsal tissue remains viable as long as the oxygen saturation index is above a value of 1. Prolonged tissue hypoxia with an oxygen saturation index below a value of 1 will result in eventual tissue necrosis. Near-IR hemoglobin oxygen saturation measurements immediately following the elevation of the flap can determine tissue in which the hemoglobin oxygen saturation is dangerously low. Additionally, the rate of change in the oxygen saturation index appears to be correlated to the rate at which tissue will become necrotic (assuming no intervention). Furthermore, near-IR monitoring of tissue post-operatively can detect vascular complication before extensive ischemic damage to the tissue has occurred.

II. Multispectral Imaging

EXAMPLE X

Skin Flap Model

The reverse McFarlane rat dorsal skin flap has long been used as a model for post-surgical tissue viability (Myers, 1987, *Adv in Plast Reconst Surg* 4:245–274). The method involves raising a long flap of skin from the dorsal surface of a rat, isolating the raised flap from the surrounding tissue except for leaving it attached at the posterior end as shown schematically in FIG. 14. This attachment forms the vascular base or pedicle of the flap. All the blood supply for the flap derives from the vascular pedicle and, in particular, the sacral vessels that are contained within the pedicle. Tissue near the vascular pedicle receives adequate blood supply and remains viable while tissue further from the pedicle is less effectively blood perfused. If the deprivation of oxygen and nutrients is severe enough and prolonged enough, the poorly perfused regions of the flap will not survived. As a model for the investigation of tissue viability, the reverse McFarlane skin flap is designed to fail somewhere near the mid-point, between the pedicle base and distal end of the flap. However, prior to 5–6 h after surgical elevation of the flap there is no visual evidence, even to a skilled clinician, of failing tissue along the length of the flap. After 6 h post-elevation of the flap, a faint demarcation line usually appears. Over the next 66 h the demarcation line moves slightly closer towards the pedicle and tissues on the side of the demarcation line proximal to the pedicle remain viable while tissues on the distal side of the demarcation line become frankly necrotic. Herein, the reverse McFarlane skin flap model is used to investigate the sensitivity of visible/near-IR multispectral imaging in detecting inadequate perfusion along the length of the flap and to determine the correlation between the regions identified by cluster analysis of 1 h post-op images with the viable and necrotic fractions of the flap as determine by visual assessment of the flap 72 h post-op.

EXAMPLE XI

Methods of Anaesthesia and Surgery

3×10 cm reverse McFarlane flaps raised on the dorsa of 4 Sprague Dawley rats, each weighing between 380–410 grams, were used. The rats were acclimatized for a minimum period of 2 weeks prior to the study and all the procedures were done under 2% isoflurane inhalational anesthesia. Five days prior to surgery, the rats were shaved, a depilatory agent (Nair™) was applied on the rat dorsum, and five reproducible anatomic landmarks along the length of the flap were marked on the skin as reference points for the multispectral images. The dorsal skin flap and anatomical landmarks are shown schematically in FIG. 14 while FIG. 15 shows a 565 nm reflectance image of a rat dorsum immediately post-surgery.

Twenty minutes prior to surgery, the rats were premedicated with 0.05 mg/kg atropine sulfate administered subcutaneously. The rats were then anesthetized and placed on a water blanket to maintain body temperature at 37° C. during surgery. Once body temperature was stable, and immediately prior to surgery, pre-elevation images were acquired. The surgery was done under aseptic techniques, a 3 cm wide and 10 cm long flap consisting of skin and underlying panniculus carnosis based on the sacral vessels was raised. The flap donor site was then closed and the flap was stretched to its original 10×3 cm dimensions and loosely sutured over the skin of the rat dorsum. The edges of the flap and the flap donor site were treated with an antibiotic ointment (Furacin) and post-operative analgesia was provided by subcutaneous injections of buprenorphine (25 $\mu$g/kg) every 12 h for the duration of the experiment. Post-operatively, multispectral images were carried out within 1 h of elevating the flap and again at 6 h post-elevation. Flaps were visually assessed for three days post-operatively, over which time the rats were housed separately. In this model, the flap derives its blood supply from two sacral vessels at the base of the flap. This base, proximal to the blood supply, is expected to be well perfused, while the distal end of the flap is poorly perfused. Any blood flowing to the distal end of the flap should also be poorly oxygenated. Thus, parameters related to tHb, tissue $O_2$sat, and hydration are expected to vary along the length of the flap. The viable fraction (outcome) of the flap was determined from the final 72 h post-elevation visual assessment after which the rat was sacrificed.

EXAMPLE XII

Visible-near Infrared Multispectral Imaging

Oxygenated hemoglobin ($HbO_2$) and deoxygenated hemoglobin (Hb) have different visible and near-IR spectra, as shown in FIG. 16. Hb has absorption maxima at 430, 555, and 760 nm while $HbO_2$ has the corresponding absorption maxima at 415, 540, 576, and 900 nm. Non-invasive monitoring of hemoglobin oxygenation exploits the differential absorption of $HbO_2$ and Hb along with the fact that near-IR radiation can penetrate relatively deeply into tissues. Clinically, pulse oximetry routinely supplies a noninvasive measure of arterial hemoglobin oxygenation based on the differential red-visible and near infrared absorption of Hb and $HbO_2$. Visible/near-IR multispectral imaging permits the regional variations in tissue perfusion to be mapped. Unlike infrared thermography, this approach does not map the thermal emission of the tissues; instead, this imaging method relies on the differential absorption of light by the Hb and $HbO_2$, resulting in differences in the wavelength dependence of the tissue reflectance depending on the hemoglobin oxygen saturation of the tissue.

The following wavelengths were chosen for imaging: 430, 565 and 760 nm, which are centred near Hb absorption maxima; 550 and 830 nm channels, which are located near Hb/$HbO_2$ isobestic points; and 980 nm, which is located at an absorbance maximum for $H_2O$. These wavelengths combine traditionally used visible information with commonly used near-IR wavelengths. The series of images obtained (430, 530, 565, 760, 830, and 980 nm) contain both spatial and spectral information. Following any given pixel through the series of images, one obtains the visible and near-IR spectral response of the sample for those wavelengths at that location.

Near infrared and visible images were collected using a Photometrics Series 200 CCD camera consisting of a 512× 512 back-illuminated CCD element and a 14-bit A/D converter (Photometrics, Tuscon, Ariz.). The images were collected as 256×256 arrays, binning the CCD in 2×2 squares. The camera was fitted with a Nikon Micro AF60 lens with the f-stop set to 8 and a Cambridge Research Instruments liquid crystal tumable filter, using 10 nm bandpass (FWHH Lyot type filters, and the dorsal surfaces of the rats were evenly illuminated using a Bencher CopyMate II copy stand equipped with quartz lamps. Wavelength selection was also performed by sequentially placing 10 nm half-width bandpass filters with maximum transmission wavelengths of 430, 550, 565, 760, 830, and 980 nm (OCLI, Santa Rosa, Calif.) in a holder in front of the lens.

EXAMPLE XIII

Image Pre-processing Methods

Prior to fuzzy C-means cluster analysis (FCM), a 5×5 median filter was applied to all images, with the exception of those images designated as being raw data. The effectiveness of log residual correction of the multispectral images and data standardization (normalization) prior to FCM cluster analysis was also investigated.

The multispectral images ($X_{ij}$ where i=pixel number and j=wavelength channel number) in this study are assumed to be the product of the wavelength response of the system ($I_j$=convolution of the spectral output of the illumination source and the wavelength response of the CCD detector) with a topographical factor related to uneven surface illumination and surface topography of the rat dorsum ($T_i$) and the tissue reflectance ($R_{ij}$).

$$X_{ij}=T_iR_{ij}I_j \qquad (1)$$

Approximate flat-surface reflectance images were obtained using the logarithmic residual method (Okada et al, 1993, *J Photogramm Remote Sensing* 48:16–27) which subtracts estimated topographical and illumination factors from the measured radiance image. The logarithmic residual method effectively mean centers the multispectral data set over both the image pixel and wavelength channel dimensions and adds the grand mean back to the resultant image, $$\log(R_{ij}) = \log X_{ij} - \frac{1}{N}\sum_i \log X_{ij} - \frac{1}{M}\sum_j \log X_{ij} + \frac{1}{NM}\sum_{i,j} \log X_{ij} \quad (2)$$

with N=total number of pixels and M=number of wavelength channels. Since the technique relies upon mean values over the pixel and wavelength channel dimensions, the resultant reflectance image is influenced by outlier radiance intensities. For this reason, median filtering was performed prior to the logarithmic residual calculations. Log residual correction has been used in remote sensing applications to compensate for uneven illumination conditions arising from curved surface topology (Myers, 1987).

Statistical scaling was used to enhance the contrast of the calculated reflectance multispectral image. Object contrast is dictated by the contrast ratio, $\sigma/\bar{R}$ where $\bar{R}$ is the average reflectance of the object, and $\sigma$ is the standard deviation of the reflectance of the object and its surroundings. Statistical scaling of the images enhances subtle variations in the spectral reflectance of the tissue and ensures that the multispectral image sequence has unity variance over each wavelength channel image. Applying the inverse contrast ratio transformation enhanced subtle variations in the spectral reflectance of the tissue and ensured that the multispectral image sequence $S_{ij}$ had unity variance over both the pixel and the wavelength channel dimensions.

$$S_{ij} = \frac{R_{ij}}{\sigma_i(R_{ij})\sigma_j(R_{ij})} \quad (3)$$

Singular value decomposition (Jackson, 1991) decomposes the multispectral reflectance image, S, into a set of eigenvectors, U and V, ($V^t$ indicates transpose of V)

$$S = U a^{1/2} V^t \quad (4)$$

which diagonalize the cross product matrices $SS^t$ and $S^tS$ respectively and are associated with the common set of eigenvalues, a. The eigenvector basis, V, spans the wavelength channel (column) space thus providing the principal component loadings for the wavelength channels (variables). The eigenvector basis, U, spans the image pixel (row) space of the original data matrix S and corresponds to the principal component scores for the images (objects).

In the multispectral images, the number of image pixels (N=65536) greatly exceeded the number of wavelength channels (M=6). Thus, the eigenvectors V (principal component wavelength loadings) of the smaller dimensional M×M (6×6 in this case) space of $S^tS$ were first calculated and used with the original data matrix, S, in conjunction with equation. 4 to reconstruct the image principal component scores, U (score images).

The normalized eigenvalue, $$p_k = \frac{a_k}{\sum_{i=1}^{q} a_i} \quad (5)$$

provides a measure of the percent variance accounted for by the $k^{th}$ principal component of the expansion of the multispectral image matrix S. Eigenvalues along with the associated eigenvectors were reordered from the largest to the smallest eigenvalue. Thus, the ordered set of q linearly independent principal components account for successively smaller fractions of the variation in the tissue reflectance. The first 3 PCs of the multispectral image accounted for more than 93% of the variance, PCs 4–6 which accounted for less than 7% of the variance typically represented noise in the multispectral image. Only the first 3 PCs of the principal component expansion of the statistically scaled log-residual corrected reflectance multispectral image were retained for further analysis.

PCA is a diagnostic method aimed at determining generalized components of variance in the data set. However, in practice, partitioning the data set into the components of maximal variance can often complicate the interpretation of the data. An orthogonal varimax rotation of a subset of the PCs into a set of new uncorrelated variables (factors) often eases data interpretation by providing a clearer pattern of wavelength loadings while explaining the same amount of variability of the data set as the subset of PCs from which they were derived (Jackson, 1991). The varimax method maximizes the objective function, $$Q = \sum_{j=1}^{k}\left[\sum_{i=1}^{M} V_{i,j}^4 - \frac{1}{M}\left(\sum_{i=1}^{M} V_{i,j}^2\right)^2\right] \quad (6)$$

where only the first k PCs (loading vectors) have been retained and the sums of squares of the squared wavelength loadings are maximized, columnwise, for the k rotated factors. Varimax rotated images were then calculated from the three varimax rotated loadings derived from the first 3 PCs of the principal component expansion of S.

All data preprocessing routines were performed using the Interactive Data Language (IDL, Research Systems Inc., Boulder, Colo.).

EXAMPLE XIV

Cluster Analysis

Unsupervised hard and fuzzy cluster analyses were used to determine the spectral response at any particular pixel of the flap and group together the pixels of the image which have similar responses. Calculation methodologies such as PCA and unsupervised cluster analysis that do not require a priori knowledge of the spectral responses of the sample are of the greatest utility, since they do not introduce bias into the analysis. Model free methods have the added advantage that unexpected as well as anticipated responses can be identified.

The ISODATA is a nearest-centroid non-hierarchical clustering algorithm consisting of a k-means clustering procedure embedded in a loop which uses cluster standard deviation thresholds and compares within cluster average distances to overall averages cluster distances to split or merge the number of clusters used in the k-means analysis.

The fuzzy C-means cluster analysis (FCA), as implemented in this study, identifies regions of tissue which have a similar spectral response by clustering the pixel-by-pixel spectral responses such that the within-group's Euclidean distance is minimized. The results include, for each cluster, the cluster centroid (i.e., the weighted mean spectrum for the cluster), and the corresponding cluster membership map (i.e., the spatial distribution of the cluster). The fuzzy C-means algorithm iterates to convergence. During each iteration, the fuzzy cluster centroids $v_{kj}$ (in this case, the spectral responses), and the fuzzy cluster memberships $U_{ki}$ are updated for each of the K clusters as follows, $$v_{kj} = \left(\sum_{i=1}^{p} (u_{ki})^m \hat{X}_{ij}\right)\left(\sum_{i=1}^{p} (u_{ki})^m\right)^{-1} \quad (7)$$

$$u_{ki} = \left(\sum_{l=1}^{K} \left(\frac{d_{ki}}{d_{li}}\right)^{2/(m-1)}\right)^{-1} \quad (8)$$

$$d_{ki} = \left(\sum_{j=1}^{M} (\hat{X}_{ij} - v_{kj})^2\right)^{1/2} \quad (9)$$

where $d_{ki}$ represents the Euclidean distance between cluster centroid k and data pixel i. The iteration process terminates when the magnitude of the change in the cluster membership values decreases below a set threshold.

Associated with each cluster there is a membership map, which contains at each pixel a membership value ranging from 0 (no membership) to 1 (full membership) for that particular cluster. The sum of all memberships for each pixel is constrained to 1. In contrast to hard clustering techniques, which only allow either a 0 (not belonging to the cluster) or 1 (belonging) membership, fuzzy memberships increase the reliability of the analysis. In this application, fuzzy clustering methods are expected to allow a more specific, hence robust, classification of the spectroscopic images compared to hard clustering methods.

All data preprocessing routines were performed using the Interactive Data Language (IDL, Research Systems Inc., Boulder, Colo.). PCA and FCA was carried out on both the raw multispectral images, logarithmic residual corrected multispectral images, as well as statistically scaled (images divided by image standard deviations) multispectral images. FCA was carried out using "Evident", version 2.3, an in-house software package developed in IDL for the analysis of temporal or spectral image data (Mansfield et al, 1997a, *Comp Med Img Graph* 21:299–308). All calculations were performed on a Silicon Graphics Challenge series server (SGI, Mountain View, Calif.).

EXAMPLE XV

Fuzzy C-means (FCM) Cluster Analysis

FCM cluster analysis was carried out on the raw multispectral images, log residual corrected multispectral images, as well as statistically scaled multispectral images. FCM cluster analysis was carried out using "Evident", version 2.3, an in-house software package (Mansfield et al, 1997a; Mansfield et al, 1997b, *Anal Chem* 69:3370–3374) developed in IDL for the analysis of temporal or spectral image data. All calculations were performed on a Silicon Graphics Challenge series server (SGI, Mountain View, Calif.).

The objective of analyzing multispectral images is not only to determine the spectral response at any particular pixel in the sample, but also to determine which regions of the sample contain similar responses. In practice, this requires the detection of distinct spectral responses in the series of the images (i.e., the spectral shape of the response), and the regions of the sample where these occur. Calculation methodologies that do not require a priori knowledge of the spectral responses of the sample are of greatest utility, since they do not introduce bias into the analysis. Since FCM cluster analysis is model-free, unexpected as well as anticipated responses can be identified. FCM cluster analysis, as implemented in this study, identifies regions of tissue that have a similar spectral response by clustering the pixel-by-pixel spectral responses such that the differences in the intra-cluster spectral responses are minimized, while simultaneously maximizing the inter-cluster differences between spectral responses. The results of this cluster analysis include, for each cluster, the cluster centroid (viz., the weighted mean spectrum for the cluster), and the corresponding cluster membership map (viz., the spatial distribution of the cluster). Taken together, they answer two commonly posed questions about spectroscopic imaging: where did the different types of spectra occur (shown by the cluster membership maps) and what were the spectral characteristics (depicted by the cluster centroids).

Associated with each cluster is a fuzzy membership map, which contains at each pixel a membership value ranging from 0 (no membership) to 1 (full membership). In contrast to hard clustering techniques, which only allow either a 0 (not belonging to the cluster) or 1 (belonging) membership, fuzzy memberships increase the reliability of the analysis. Hard classifiers, such as k-means or nearest neighbour clustering methods, do not allow for membership in multiple clusters. Fuzzy C-means clustering allows each unit being clustered to have membership in more than one cluster.

Prior to clustering, a region of interest (ROI) is selected. The entire image, some smaller subset(s) of the entire image (usually the region of the image containing the skin flap), and subsets of the multispectral imaging sequence were selected. The FCM clustering analysis was performed only on those spectra inside the selected ROI.

All of the calculations were repeated for all four flaps and consistent results were achieved across all of the flaps.

EXAMPLE XVI

Results and Discussion

FIG. 16 shows the visible—near infrared absorption spectra of hemoglobin (Hb), oxy-hemoglobin ($HbO_2$) and water ($H_2O$), as well as the wavelength channels used in the multispectral image sequence. The six wavelength channels selected for the multispectral images closely correspond to absorption band maxima or isobestic points for Hb, $HbO_2$ or $H_2O$ (Cordone, 1986; Eaton and Hofrichter, 1981). The 430, 565 and 760 nm channels closely correspond to absorption maxima of Hb, the 550 and 830 nm channels are near Hb/$HbO_2$ isobestic points (where Hb and $HbO_2$ absorb equally), while the 980 nm channel lies on the absorption maximum of $H_2O$. Spatial variation in tissue blood volume results in a corresponding variation in the tissue reflectance at the wavelengths where Hb, $HbO_2$ and $H_2O$ have a significant absorption. Spatial variation in hemoglobin oxygen saturation results in a change in the differential reflectance at absorption wavelengths associated with $HbO_2$ relative to wavelengths where Hb preferentially absorbs. However, reflectance intensity at isobestic wavelengths are unaffected by spatially varying oxygen saturation. Changes which are observed at the 980 nm water absorption band but which do not correlate with observations at the Hb/$HbO_2$ isobestic reflectance wavelength arise from changes in tissue hydration (edema) which are independent of blood volume changes. Images based on the selected wavelengths can thus provide a measure of the blood volume or total hemoglobin (tHb), the fraction of oxygenated hemoglobin ($O_2$sat) and the relative degree of tissue hydration.

FIG. 14 illustrates the dorsal reversed McFarlane skin flap model used. In this model, three sides of the flap are incised while one end, termed the vascular pedicle or base, contains the sacral vessels and is left attached to the remaining skin. After surgically raising the flap to its base, the underlying wound is stitched closed. The flap is then laid back down and loosely attached over the closed wound, The five sites at which spectroscopic measurements are taken are marked with an indelible red pen, and, as a result, are only seen in those images acquired in the visible region. The reverse McFarlane flap derives its blood supply from two sacral vessels at the base of the skin flap. The base of the flap, proximal to the blood supply, is expected to be well perfused while the distal end of the flap is poorly perfused. Any blood flowing to the distal end of the flap should also be poorly oxygenated. Thus parameters related to tHb, tissue $O_2$sat, and hydration are expected to vary along the length of the flap.

EXAMPLE XVII

Raw Images

The upper panel of FIG. 17 shows multispectral radiance images of the rat dorsum taken immediately following surgical elevation of the skin flap. FIG. 18 compares near infrared spectra taken at the same time point and from the same flap as presented in FIG. 17. The solid trace spectrum is taken near the distal end of the flap (site 5) while the dashed spectrum arises from near the base of the flap (site 1). The imaging wavelength channels are overlayed on the spectra in FIG. 18. Comparison of the raw wavelength channel radiance images in the upper panel of FIG. 17, generally reveals little or no contrast along the length of the flap. The 430 nm channel does provide some limited contrast between the distal end of the flap and its base. This channel is centered on the Soret (B-band) absorption band region of Hb and $HbO_2$ (see FIG. 16) as well as being influenced by skin pigmentation absorptions. A comparison of the spectra presented in FIG. 18, reveals that the distal end of the flap is slightly less reflective (stronger absorption) relative to the base of the flap. Thus the base of the flap in the 430 nm channel appears brighter than the more distal zones of the flap. (Note that diffuse reflectance spectra are plotted in the usual log(1/R) scale where R is the tissue reflectance).

The 550 nm channel is centered on the isobestic point between the $Q_v$ vibronic transition band maxima of Hb and $HbO_2$. The 565 nm channel lies between the $Q_v$ and $Q_o$ absorption bands of $HbO_2$, at a point of minimum absorption for $HbO_2$, but centered on the shoulder of the $Q_v$ absorption maximum of Hb. Neither of these channels display significant contrast in the images nor do the spectra between the base and distal site show significant differences in the absorption over those imaging wavelength regions. The 550 nm channel might be expected to be sensitive to overall blood volume changes since both Hb and $HbO_2$ contribute equally to the tissue absorption at this wavelength while the 565 nm channel might be expected to distinguish regions of varying tissue hemoglobin oxygen saturation. However, the 550 and 565 nm channel images are highly correlated (r=0.96) and essentially provide redundant information. Table 3 lists the correlation coefficients between the wavelength channel images averaged over the multispectral images taken immediately post-operatively of four different reversed McFarlane rat dorsal skin flaps. The high degree of overlap between the Hb and $HbO_2$ absorptions in the visible region, see FIG. 16, gives rise to the high correlation between the visible wavelength channels.

Based on the spectra in FIG. 18, the differential reflectance at 760 nm between the base and the distal end of the flap was expected to provide reflectance images with significant tissue contrast along the length of the flap. Since the 760 nm imaging channel is centered on the III charge transfer band of Hb with little underlying $HbO_2$ absorption, tissue contrast provided by this channel can be related to the Hb distribution within the flap. The 830 nm channel which is near an Hb/$HbO_2$ isobestic point was expected to be sensitive to blood-volume variations but provide poor contrast due to near equal reflectance from the base and distal zones of the flap. Neither the 760 nor the 830 nm channel in the raw radiance images provided significant contrast along the skin flap. Although these near infrared channels were poorly correlated with the visible channels (r≦0.68), the 760 and 830 nm reflectance channels were significantly correlated (r=0.85) with each other and provided limited information on the skin flap perfusion.

The 980 nm channel was chosen in the multispectral imaging sequence to provide water related information. This wavelength channel is centered on a near infrared $H_2O$ absorption band. The 980 nm channel is poorly correlated with the other wavelength channels and displays a weak intensity gradient from the base of the flap extending to the distal end of the flap with the distal zone being more reflective at this wavelength. Careful examination of the spectra in FIG. 18 reveals a slightly stronger absorption in the 980 nm region in the spectrum taken near the base of the flap which is consistent with the darker appearance of the flap base in the 980 nm image channel.

EXAMPLE XVIII

Image Pre-processing Techniques

The poor contrast in the original radiance images prompted us to use contrast enhancement. In addition, shadowing artifacts in the radiance images due to the uneven surface topography of the rat dorsum and uneven surface illumination tended to obscure distinguishing features along the length of the flap. Logarithmic residual correction largely eliminated these image artifacts. Furthermore, statistically scaling the log-residual corrected reflectance images significantly improved image contrast along the length of the skin flap (lower panels of FIG. 17) for most of the wavelength channels, most notably at the 550, 565 and 980 nm channels. After the logarithmic residual correction, the 550, 565 and 760 nm image channels displayed the lowest standard deviation. Statistical scaling by $\sigma_t(R_{ij})$, therefore, enhanced the intensity of these wavelength channels over the remaining channels. The local standard deviation of the base of the flap is greater than that toward the distal end of the flap, thus statistically scaling the images to local standard deviations $\sigma_l(R_{ij})$ tends to enhance contrast between the base and distal region of the flap in the wavelength channels which displayed limited contrast in the original data set. For instance, the 550 and 565 nm channels display a reflectance gradient along the length of the flap with the distal section of the flap being less reflective relative to the base of the flap and the surrounding uninvolved tissue which is a consequence of the stronger absorption of these wavelengths by the distal portion of the flap.

The 760 and 830 nm channels, when statistically scaled, reveal subtle differences in the tissue reflectance at these wavelengths. At 760 nm, the distal section of the flap shows a reduced reflectance compared to the flap base while at 830 nm the distal half of the flap shows a slight increase in reflectance over the flap base and surrounding uninvolved tissue. Due to the large differential absorption of Hb and $HbO_2$ at 760 nm and their near equal absorption at 830 nm, these results suggest a comparatively lower tissue hemoglobin oxygen saturation in the distal half of the flap as well as a concomitant decrease in blood volume over the distal half of the flap.

Contrast in the 980 nm wavelength channel is particularly enhanced by statistical scaling due to the small spatial standard deviation in the 980 nm reflectance image. The 980 nm reflectance of the surrounding, uninvolved, dorsal tissue is comparable to the base of the flap. This indicates a marked difference in the reflectance at 980 nm between the distal half of the flap which is poorly perfused in this model and the remainder of the dorsal tissue. The lower water content in the distal half of the flap which arises from the limited perfusion of this zone results in less water being able to absorb the incident 980 nm light and thus an increased reflectance of this wavelength from the distal half of the flap.

EXAMPLE XIX

Principal Component Analysis

A number of the wavelength channels are highly correlated suggesting that a truncated PC expansion could effectively provide the relevant tissue perfusion information in a more compact and significantly higher signal to noise representation. PCA of the statistically scaled logarithmic residual reflectance images decomposes the multispectral image sequence into a set of uncorrelated PCs. Table 4a reports the percentage of the variance and the loadings of the individual wavelength channels for each PC averaged over the four flaps used in this study. The first three PCs accounted for more than 93% of the variance in the multispectral sequence. The higher order PCs which account for less than 7% of the variance represented noise and thus only the first 3 PCs were retained in the PCA expansion. A representative set of the first three PC images are presented in FIG. 19, upper panel. The first PC which is dominated by the positive loading (0.72) from the 430 nm wavelength channel, also has significant contributions from the 980, 760 and 830 nm channels (see Table 4a). Contrast along the flap is particularly evident in the second PC, again a number of wavelength channels contribute significantly to this PC, however, it is the 980 nm channel that has the largest absolute loading (−0.70) in this PC. The third PC shows little contrast over the rat dorsum and has complicated pattern of loadings. Having a number of wavelength channels contributing to each PC complicates the interpretation of the PC images. Varimax rotation of these PCs simplifies image interpretation.

The primary aim of the varimax method is to rotate the factors in such a way that the new loadings tend to be either relatively large or small in absolute magnitude compared with the originals. A distinct pattern of loadings can thus be obtained since factors are marked by high loadings for some wavelength channels and low loadings for others. Table 4b lists the wavelength channel loadings for the varimax rotated factors derived from the first 3 PCs, the corresponding varimax rotated images are presented in the lower panel of FIG. 19. Based on the loadings varimax rotated images are somewhat easier to interpret compared to unrotated PCs. The 430 nm channel dominates the first rotated component and thus it resembles the statistically scaled 430 nm channel with an improved signal—to—noise level. The absolute value of the 980 nm channel loading dominates the second factor. Thus, as expected, this factor closely corresponds to the negative of the 980 nm statistically scaled image in FIG. 17 and maps flap water content which in turn should track the blood volume of tissue. In the third rotated component, 430 and 980 nm make only a minor contribution to the factor which is effectively a 760, 830 nm near infrared—550, 565 nm visible difference image. This factor compares to the response from a clinical oximeter which measures the difference between the reflectance of a visible light emitting diode (LED) and a near infrared LED. This difference is related to the fraction of oxygenated hemoglobin ($O_2$sat). The third factor should therefore weight the Hb/$HbO_2$ distribution in the flap with the regions with a lower fraction of oxygenated hemoglobin appearing brighter in the varimax image.

EXAMPLE XX

Hard K-means Clustering Analysis

Regional segmentation of multispectral images was done using a hard k-means clustering procedure embedded in an ISODATA algorithm. ISODATA selects the number of image clusters based on clusters standard deviation thresholds and compares within cluster average distances to overall average cluster distances. ISODATA hard k-means cluster analysis of logarithmic residual corrected multispectral images indicated four major regions displaying distinct multispectral responses immediately after surgical elevation of the skin flap. The four-cluster membership map is presented in FIG. 20.

EXAMPLE XXI

Fuzzy C-means Clustering Analysis

Based on the number of clusters selected by the ISODATA image spectral clustering, multispectral images were segmented into four clusters using a fuzzy C-means cluster analysis (FCA) algorithm. The cluster membership map and centroid multispectral responses are presented in FIG. 21, with the color of the membership region corresponding to the color of the centroid spectrum. The regions associated with each fuzzy cluster correlate closely with a particular hard cluster region determined using k-means clustering. However, fuzzy clusters generally had continuous boundaries while in the transitional region of the flap hard clusters generally have some membership pixels isolated within the boundaries of a different cluster. Given the failure pattern of the skin flap in this model, the FCA provided superior regional segmentation of the multispectral images of the post-operative skin flap tissues compared to hard k-means cluster analysis.

In order to determine the inter-animal reproducibility of the results, FCA was applied to the multispectral image sets pooled over all animals used in the study (n=4). The spectra pooled from the 4 image sets were segmented into locally optimal 2, 3 and 4 cluster analyses. For clarity, only the 2 cluster results are presented in FIG. 20. The upper panel of FIG. 20 shows the cluster membership maps overlaid on an anatomical image. FCA of the logarithmic residual corrected multispectral images clearly distinguishes the poorly perfused distal section of the flap (FIG. 20, red) from the well-perfused proximal portion of the flap (FIG. 20, green). The segmented membership regions closely correlate with the failure patterns of the individual animals. The bottom panel of FIG. 20 shows the centroid spectrum from the two regions of each of the subjects. The color of the trace indicates to which cluster the spectrum belongs, and the number used as a symbol for each data point corresponds to the flap from which the spectrum was derived. The inter-animal variability in the multispectral response from the flap is significantly smaller than the spatial variability within the flap.

FIG. 23 shows the results of clustering the spectra from the dorsal flap of rat 1 into three clusters. For FIG. 23A, all six wavelength images were used in the calculation. FIG. 23B shows the results using only the near-IR wavelengths (760, 830, and 980 nm), and FIG. 23C shows the results using only the visible wavelengths (430, 550, and 565 nm). For each of these calculations, the spectra were normalized by subtracting the mean value and dividing by the standard deviation for each spectrum. This spectral normalization makes the clustering algorithm less sensitive to changes only in absolute intensity and more sensitive to changes in bandshape and relative intensity. Without using some form of normalization, the spectra did not cluster into regions of physiological significance; rather, they clustered according to the intensity of the reflectance profile, which is governed, in general, by both the intensity of the illumination and the curvature of the sample at any given point. The upper panel of FIG. 23A shows a 565 nm reflectance image of rat 1 with the clustering results superimposed. The color of the region corresponds to the colour of the spectral response trace shown in the lower panel. The region displayed in the green cluster in FIG. 23A (upper) corresponds to the end of the flap nearest the vascular base of the skin flap. Its proximity to the vascular base suggests that this region of the flap should remain well perfused throughout the experiment and remain viable over the clinical course of the skin flap. The region displayed in the red cluster is further removed from the vascular base of the flap and thus receives inadequate blood supply. This poorly perfused region becomes non-viable over the intervening 72 h post-operative clinical monitoring period. The yellow regions correspond to the areas where surgical ink was applied to the surface of the flap prior to surgery as visual reference points. The centroid spectra (lower panel FIG. 23A) indicate the mean spectral reflectance response from the specific cluster. The major difference between the centroid spectra from the clusters corresponding to the region of the flap near the base (green, FIG. 23A) and distal from the vascular base (red, FIG. 23A) is in the reflectance intensities in the near infrared at 830 and 980 nm. The green cluster, which comprises tissue near the vascular base of the flap, is less reflective at both 830 and 980 nm compared with that of the red cluster. Since oxyhemoglobin and water dominate tissue absorption at 830 and 980 nm, respectively, the lower reflectivity at both 830 and 980 nm at the base of the flap relative to the distal portion of the flap suggests the presence of more oxygen and more fully hydrated tissue near the vascular base of the flap. This is consistent with the superior blood perfusion of tissue nearer the vascular base of the flap compared to the tissue more distal to the blood supply.

The relative contributions of the visible and near-IR wavelengths to the FCM clustering results were determined by comparing the FCM cluster analysis results when using only the visible wavelength channels with the FCM clustering results for which the analysis included only near-IR wavelength channels. FIG. 23B displays the results of the clustering analysis using only the near-IR wavelengths, and FIG. 23C shows the results of the clustering analysis using only the visible wavelengths. FIG. 23A, again, clearly shows the division into well-perfused and poorly perfused regions of tissue as well as the regions with the surgical ink reference points. FIG. 23B shows a more diffuse differentiation of flap tissue perfusion, but one which is generally similar to that of FIG. 23A. The region shown in yellow indicates generally where the tissue is well perfused and remain viable while the regions shown in red and green demarcate those regions which are poorly perfused and became non-viable. As in FIG. 23A, the major difference between the centroid spectra of the yellow and the green and red regions in FIG. 23B is in the reflectance intensity at 830 and 980 nm, with the region corresponding to the well perfused region (yellow) having less reflectance intensity and, hence, more oxyhemoglobin than the other regions. The red, green, and yellow regions in FIG. 23C correspond to the fuzzy C-means clusters when only the visible wavelength channels were included in the analysis. These cluster regions show little or no correlation with the perfusion status of the skin flap but do display a correlation with the visible ink marks drawn on the flap.

The efficacy of three simple image preprocessing steps in recovering clinically useful information from the FCM cluster analysis of the multispectral images was investigated by Median filtering (5×5 window), log residual scaling, and statistical scaling of the multispectral image sequences prior to FCM cluster analysis, with the results being compared in FIG. 24. FIG. 24 shows the results of clustering the preprocessed multispectral images of the flap from the same rat into three clusters using the four different preprocessing steps. FIG. 24A shows the results from the raw data, FIG. 24B shows the results from the median filtered data set, FIG. 24C shows the results from the Log Residual data set, and FIG. 24D shows the results from the Statistically Scaled data set. The clustering results in FIGS. 24A and 24B clearly have no correlation with flap tissue perfusion, and FIG. 24B, as is expected, appears to be a smoothed version of FIG. 24A. FIGS. 24C and 24D, on the other hand, show regions which correlate with the extent of flap tissue perfusion. In both cases, the regions shown in green correlate with the regions of tissue which is well perfused in this flap model, while regions shown in red or yellow correlate with poorly perfused regions of tissue or those regions containing the ink visual reference marks. The log residual image set and the statistically scaled data set gave very similar results for these clustering analyses, despite the fact that the extra statistical scaling step has helped for other analysis methods. The regions shown in red and yellow in FIGS. 24C and 24D have nearly identical centroid spectra, both of which are easily differentiable from the centroid spectra of the regions shown in green.

Given that the log residual images and the statistically scaled images gave similar clustering results, the log residual image set was chosen for the final clustering methodology. FIG. 25 shows the results of clustering the log residual pre-processed multispectral images pooled over all of the four rats. FCM cluster analysis was used to partition the pooled multispectral image data set into two clusters. No extra normalization was used beyond the log residual calculations. The pixel-based cluster membership map obtained from the FCM analysis of the pooled images was fragmented into the individual map for each flap. The upper part of FIG. 25 shows the individual cluster membership maps for each of the four skin flaps which were derived from the FCM analysis of the pooled multispectral images from the four flaps. The middle section of FIG. 25 shows color images of the 72 h end point of the experiment with viable and non-viable sections of the flap clearly identifiable. The lower part of the FIG. 25 shows the centroid spectra from each of the clusters and flaps. The color of the trace denotes from which cluster the spectrum came and the numbers representing each data point denote the rat from which the spectrum came. The regions and spectra shown in green correspond closely with regions of tissue which are well perfused and that remain viable over the 72 h clinical time course of the flap. The regions and spectra shown in red correspond closely with the poorly perfused regions of flap tissue. It is these distal regions of the skin flap which fail over the intervening 72 h monitoring period. The red and green centroid spectra clearly show differences between the viable and non-viable regions of the flap, with spectra from viable regions (green) having relatively less reflectance intensity for the 830 and 980 nm points and relatively more reflected intensity at the visible wavelength channels (430, 550, and 565 nm). As these spectra originate from images which have undergone the log residual image processing, the centroid spectra for the clusters cannot be compared directly in the same manner raw reflectance data can. However, the relative intensities are consistent with the viable portions of the flap (proximal) containing more oxygenated hemoglobin and water than the non-viable portions (distal) as was seen in the single flap analysis (see FIG. 23A for comparison).

In analyzing the results of clustering the spectra from 4 flaps (upper panel, FIG. 25), where the multispectral near-IR images were taken within one hour of the surgery and the color image at the 72 h endpoint of the experiment (middle panel, FIG. 25), there is a clear correlation between the regions selected by the FCM analysis and visual inspection of the color images. In some cases (e.g. Flap 2), the boundary selected by the FCM analysis follows the general shape and location of the boundary seen in the 72 h reference image. However, since all the spectra from the 4 flaps were pooled prior to the FCM analysis, the boundaries do not exactly match. Minor variations from flap to flap could account for the differences. It is of note that using a larger number of clusters may improve the results.

Despite the lack of an exact match between the 1 h prediction of viable and non-viable tissue and the actual 72 hour outcome, it is clear that there is a high degree of correlation between the regions selected by the fuzzy C-means algorithm on the 1 h post-surgery images and the visual diagnosis based on the 72 h clinical outcome. This correlation with the eventual clinical outcome of the flaps is particularly impressive considering that there is no clinical sign of tissue compromise until at least 5–6 h post-surgery. The log residual data pre-treatment reduces the usually large inter-subject variability of near-IR methodologies and enables the clustering algorithm to distinguish between regions of poor perfusion across the flaps of four individuals.

Conclusion

Near-infrared spectroscopy was used to monitor the oxygen delivery along a raised pedicled flap. These measurements were accomplished by determining the relative change in the deoxyhemoglobin and oxyhemoglobin concentrations. within 1 h post-operatively, spectroscopic measurements revealed a significant drop in the tissue hemoglobin oxygen saturation. The saturation drop was most pronounced in the distal half of the flap while the region nearest the base of the flap displayed the least drop in hemoglobin oxygen saturation. The hemoglobin oxygen saturation of tissue proximal to the base of the flap recovered and exceeded pre-elevation values within 6 h after raising the flap. Except for its base, the flap remained hypoxic for the remainder of the experiment. Tissues which remained below a certain hemoglobin oxygen saturation threshold (oxygen saturation index<1) for prolonged periods (>6 h) became visibly necrotic over the 72 h monitoring period. Tissues above a hemoglobin oxygen saturation threshold (oxygen saturation index>1), despite being significantly hypoxic relative to the pre-elevation saturation values, remained viable over the full 72 h post-elevation monitoring period. Prolonged and severe tissue hypoxia results in tissue necrosis in pedicled flaps. Near-infrared spectroscopy not only identifies regions of tissue with challenged oxygen supply, but also can be used to determine the severity of this challenge. Near-infrared spectroscopic monitoring of tissues at risk can be performed post-operatively, or concurrently with pharmaceutical or surgical interventions aimed at salvaging these stressed tissues, to monitor their benefit.

From these observations it is quite clear that infrared spectroscopy fulfills many of the criteria of an ideal test to predict skin viability. Data were acquired simply, rapidly and non-invasively. Measurements are consistent and reproducible with minimal inter- or intra-observer variation, and the collection of data does not pose any hazard to the tissue being studied. Even more exciting is the ability to reliably diagnose problems before they become clinically apparent and institute corrective measures.

Furthermore, by exploiting the reflectance intensity at the $Hb/HbO_2$ isobestic wavelength as a reference and using reflectance intensities centred about the short and long wavelength sides of the isobestic point, reliable measures of tissue hemoglobin oxygen saturation can be obtained from broad-band near infrared diffuse reflectance spectra or multiwavelength near infrared reflectance images. Relative measures of Hb and $HbO_2$ concentrations or oxygen saturation indices derived from these relative concentrations can be used to assess changes in tissue perfusion, specifically, oxygenation following surgical elevation of dorsal reversed McFarlane skin flaps in the rat. The degree of tissue oxygenation following surgery was found to correlate with the clinical outcome of the tissue. Thus, in the absence of surgical or pharmacological intervention, tissue oxygen saturation indices can be used to predict tissue viability following elevation of the reversed McFarlane skin flap. Clinical signs which arise as a consequence of poor blood perfusion become evident only after several hours of compromised perfusion. Oxygen saturation images, however, can provide the surgeon with almost instantaneous feedback on the perfusion status of a skin flap or graft. Early, nonsubjective detection of poor tissue oxygenation following surgery should increase the likelihood that intervention aimed at saving the tissue will be successful and thus lead to improved clinical outcome in both skin flap and grafts.

Furthermore, by exploiting isobestic wavelengths and wavelengths at which Hb, $HbO_2$ and $H_2O$ have significant differential absorptions, multivariate analysis of visible—near infrared multispectral images can be used to assess tissue perfusion, oxygenation and hydration following surgical elevation of dorsal reversed McFarlane skin flaps in the rat. Original radiance images provide poor tissue contrast along the length of the flap. However, the use of statistical scaling in conjunction with the logarithmic residual correction method makes it possible to extract valuable information that is otherwise difficult to detect. Further enhancement is achieved with PCA as it allows for the selective removal of those PCs that provide redundant information or contribute to image noise. A truncated PC expansion, therefore, provides the relevant tissue perfusion information in a more compact manner with greater signal to noise ratio while varimax rotation of the selected PCs simplifies data interpretation.

The image processing methods presented herein described are easily programmed and rapid in their execution. The acquisition and analysis of data could, therefore, be easily performed within the surgical session to provide the surgeon with immediate feedback regarding the probable future status of the tissue being examined. We conclude that multivariate analysis of multispectral images of skin tissues can potentially provide clinically relevant information on tissue perfusion in a manner that is both rapid and reliable.

A fuzzy C-means clustering methodology was used to investigate multispectral near-IR and visible images of a reverse McFarlane rat dorsal skin flap model: Multispectral images were taken 1 h post-surgery and the results of the clustering analyses were compared with the 72 h clinical outcome of the flaps. Current clinical methods require 6–12 h post-surgery before determining a prognosis. Using a combination of fuzzy C-means clustering and multispectral images, a prognosis with an excellent correlation to the 72 h outcome could be made 1 h post-surgery. Various image-processing methodologies can improve the prediction: log residual correction produces good results, while statistical scaling of the data does not significantly improve the results beyond what was found for the log residual correction. Both visible and near-IR wavelength images are required for an optimal prediction using this data set. However, taken independently, the visible wavelength images produced no correlation with outcome while the near-IR wavelength images produced a good correlation although not as clear as with both near-IR and visible wavelengths together. The log residual data correction produces data sets with a low inter-subject variability. Spectra from 1 h images can be clustered across 4 skin flaps with an excellent correlation with the final clinical outcome, this enabling the differentiation of regions of poor perfusion from regions of good perfusion. This level of inter-subject reproducibility is critical in the development of this methodology as a clinical tool; an early prognostic indicator such as this would allow surgeons to intervene, either pharmacologically or surgically, at a much earlier stage, greatly increasing the chances of successfully salvaging compromised microvascular tissue transfers.

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

TABLE 1

Mean (SD) oxygen saturation index, pooled pre-elevation measurements, immediately pre-elevation (t = 0) and at 1, 6 and 12 h post flap elevation.
* = pooled measurements for the 72 pre-operative h for which control measurements were obtained

| TIME (h.) | Pre-Op* | | 0 | | 1 | | 6 | | 12 | |
|---|---|---|---|---|---|---|---|---|---|---|
| ANIMAL # | Means | (SD) | Means | (SD) | Means | (SD) | Means | (SD) | Means | (SD) |
| Table 1a: Site 1 (Proximal site) | | | | | | | | | | |
| 1 | 1.048 | (.005) | 1.0513 | (.0003) | 1.0432 | (.0003) | 1.0483 | (.0001) | 1.0477 | (.0001) |
| 2 | 1.040 | (.002) | 1.0362 | (.0002) | 1.0311 | (.0002) | 1.0496 | (.0001) | 1.0593 | (.0002) |
| 3 | 1.042 | (.003) | 1.0419 | (.0001) | 1.0374 | (.0001) | 1.0484 | (.0001) | 1.0353 | (.0013) |
| 4 | 1.033 | (.003) | 1.0323 | (.0002) | 1.0302 | (.0001) | 1.0396 | (.0010) | 1.0272 | (.0010) |
| 5 | 1.033 | (.005) | 1.0391 | (.0002) | 1.0384 | (.0007) | 1.0455 | (.0001) | 1.0498 | (.0002) |
| 6 | 1.032 | (.003) | 1.0313 | (.0001) | 1.0230 | (.0003) | 1.0267 | (.0046) | 1.0358 | (.0008) |
| 7 | 1.029 | (.002) | 1.0292 | (.0002) | 1.0264 | (.0003) | 1.0405 | (.0003) | 1.0414 | (.0004) |
| 8 | 1.033 | (.002) | 1.0365 | (.0005) | 1.0259 | (.0005) | 1.0443 | (.0002) | 1.0359 | (.0004) |
| 9 | 1.038 | (.003) | 1.0397 | (.0005) | 1.0222 | (.0007) | 1.0500 | (.0001) | 1.0393 | (.0004) |
| All Groups | 1.037 | (.007) | 1.037 | (.006) | 1.031 | (.007) | 1.044 | (.007) | 1.041 | (.009) |
| Table 1b: Site 2 | | | | | | | | | | |
| 1 | 1.055 | (.005) | 1.0560 | (.0001) | 1.0384 | (.0005) | 1.0243 | (.0007) | 1.0170 | (.0004) |
| 2 | 1.043 | (.003) | 1.0396 | (.0003) | 1.0041 | (.0009) | 1.0230 | (.0006) | 1.0371 | (.0003) |
| 3 | 1.045 | (.002) | 1.0465 | (.0004) | 1.0154 | (.0002) | 1.0115 | (.0010) | 1.0042 | (.0017) |
| 4 | 1.042 | (.002) | 1.0405 | (.0002) | 1.0071 | (.0005) | 1.0113 | (.0020) | 1.0144 | (.0011) |
| 5 | 1.036 | (.005) | 1.0407 | (.0010) | 1.0123 | (.0006) | 1.0159 | (.0002) | 1.0109 | (.0004) |
| 6 | 1.037 | (.003) | 1.0353 | (.0001) | 0.9904 | (.0007) | 0.9835 | (.0007) | 0.9864 | (.0011) |
| 7 | 1.033 | (.003) | 1.0313 | (.0001) | 1.0120 | (.0001) | 0.9962 | (.0002) | 0.9991 | (.0009) |
| 8 | 1.042 | (.004) | 1.0409 | (.0030) | 1.0098 | (.0008) | 1.0077 | (.0006) | 1.0183 | (.0007) |
| 9 | 1.040 | (.003) | 1.0416 | (.0003) | 1.0081 | (.0009) | 1.0367 | (.0002) | 1.0311 | (.0002) |
| All Groups | 1.041 | (.007) | 1.041 | (.007) | 1.011 | (.012) | 1.012 | (.015) | 1.013 | (.015) |
| Table 1c: Site 3 (Central site) | | | | | | | | | | |
| 1 | 1.053 | (.005) | 1.0543 | (.0007) | 0.9985 | (.0024) | 0.9866 | (.0018) | 0.9920 | (.0034) |
| 2 | 1.043 | (.004) | 1.0373 | (.0002) | 0.9766 | (.0009) | 0.9858 | (.0003) | 0.9869 | (.0004) |
| 3 | 1.043 | (.002) | 1.0399 | (.0011) | 0.9924 | (.0006) | 0.9842 | (.0020) | 0.9745 | (.0005) |
| 4 | 1.043 | (.004) | 1.0407 | (.0002) | 0.9888 | (.0002) | 0.9889 | (.0004) | 0.9901 | (.0001) |
| 5 | 1.037 | (.005) | 1.0427 | (.0001) | 0.9936 | (.0010) | 0.9822 | (.0003) | 0.9853 | (.0007) |
| 6 | 1.034 | (.004) | 1.0341 | (.0009) | 0.9904 | (.0007) | 0.9912 | (.0005) | 0.9721 | (.0004) |
| 7 | 1.032 | (.004) | 1.0276 | (.0001) | 0.9878 | (.0002) | 0.9716 | (.0002) | 0.9723 | (.0002) |
| 8 | 1.047 | (.004) | 1.0503 | (.0002) | 0.9944 | (.0016) | 0.9835 | (.0001) | 0.9902 | (.0006) |
| 9 | 1.050 | (.004) | 1.0580 | (.0003) | 0.9959 | (.0008) | 1.0117 | (.0005) | 1.0054 | (.0004) |
| All Groups | 1.042 | (.008) | 1.043 | (.009) | 0.991 | (.006) | 0.987 | (.010) | 0.985 | (.011) |
| Table 1d: Site 4 | | | | | | | | | | |
| 1 | 1.049 | (.005) | 1.0496 | (.0004) | 0.9952 | (.0015) | 0.9980 | (.0005) | 0.9932 | (.0013) |
| 2 | 1.036 | (.004) | 1.0319 | (.0006) | 0.9732 | (.0004) | 0.9694 | (.0002) | 0.9721 | (.0006) |
| 3 | 1.039 | (.003) | 1.0379 | (.0004) | 0.9803 | (.0003) | 0.9589 | (.0013) | 0.9325 | (.0002) |
| 4 | 1.043 | (.003) | 1.0407 | (.0007) | 0.9840 | (.0009) | 0.9950 | (.0015) | 0.9823 | (.0009) |

TABLE 1-continued

Mean (SD) oxygen saturation index, pooled pre-elevation measurements, immediately pre-elevation (t = 0) and at 1, 6 and 12 h post flap elevation.
* = pooled measurements for the 72 pre-operative h for which control measurements were obtained

| TIME (h.) | Pre-Op* | | 0 | | 1 | | 6 | | 12 | |
|---|---|---|---|---|---|---|---|---|---|---|
| ANIMAL # | Means | (SD) | Means | (SD) | Means | (SD) | Means | (SD) | Means | (SD) |
| 5 | 1.035 | (.004) | 1.0393 | (.0003) | 0.9866 | (.0002) | 0.9773 | (.0004) | 0.9814 | (.0010) |
| 6 | 1.033 | (.004) | 1.0303 | (.0004) | 0.9994 | (.0007) | 0.9543 | (.0005) | 0.9441 | (.0004) |
| 7 | 1.030 | (.004) | 1.0256 | (.0003) | 0.9756 | (.0001) | 0.9816 | (.0005) | 0.9630 | (.0006) |
| 8 | 1.040 | (.005) | 1.0422 | (.0003) | 0.9997 | (.0010) | 0.9521 | (.0005) | 0.9274 | (.0004) |
| 9 | 1.046 | (.004) | 1.0486 | (.0003) | 0.9938 | (.0004) | 0.9991 | (.0011) | 0.9984 | (.0010) |
| All Groups | 1.038 | (.007) | 1.038 | (.008) | 0.988 | (.010) | 0.976 | (.018) | 0.966 | (.025) |

Table 1e: Site 5 (Distal site)

| 1 | 1.045 | (.004) | 1.0466 | (.0003) | 0.9897 | (.0014) | 0.9578 | (.0005) | 0.9487 | (.0001) |
|---|---|---|---|---|---|---|---|---|---|---|
| 2 | 1.037 | (.003) | 1.0342 | (.0010) | 0.9688 | (.0006) | 0.9408 | (.0002) | 0.9282 | (.0002) |
| 3 | 1.036 | (.004) | 1.0365 | (.0036) | 0.9714 | (.0014) | 0.9153 | (.0005) | 0.9246 | (.0005) |
| 4 | 1.032 | (.004) | 1.0309 | (.0006) | 0.9888 | (.0012) | 0.9339 | (.0001) | 0.9399 | (.0003) |
| 5 | 1.032 | (.005) | 1.0387 | (.0003) | 0.9759 | (.0001) | 0.9502 | (.0001) | 0.9449 | (.0002) |
| 6 | 1.026 | (.004) | 1.0295 | (.0005) | 0.9930 | (.0008) | 0.9400 | (.0009) | 0.9462 | (.0004) |
| 7 | 1.031 | (.003) | 1.0288 | (.0003) | 0.9802 | (.0022) | 0.9321 | (.0003) | 0.9209 | (.0003) |
| 8 | 1.037 | (.008) | 1.0297 | (.0005) | 0.9919 | (.0008) | 0.9401 | (.0003) | 0.9361 | (.0003) |
| 9 | 1.046 | (.006) | 1.0524 | (.0010) | 0.9920 | (.0026) | 0.9113 | (.0012) | 0.8940 | (.0014) |
| All Groups | 1.035 | (.008) | 1.036 | (.008) | 0.984 | (.009) | 0.936 | (.014) | 0.931 | (.017) |

TABLE 2

Mean (SD) tissue hydration index, pooled pre-elevation measurements, immediately pre-elevation (t = 0) and at 1, 6 and 12 h post flap elevation.
* = pooled measurements for the 72 pre-operative h for which control measurements were obtained

| TIME (h.) | Pre-Op* | | 0 | | 1 | | 6 | | 12 | |
|---|---|---|---|---|---|---|---|---|---|---|
| ANIMAL # | Means | (SD) | Means | (SD) | Means | (SD) | Means | (SD) | Means | (SD) |

Table 1a: Site 1 (Proximal site)

| 1 | 1.190 | (.010) | 1.2078 | (.0005) | 1.2050 | (.0001) | 1.2282 | (.0010) | 1.2055 | (.0005) |
|---|---|---|---|---|---|---|---|---|---|---|
| 2 | 1.169 | (.005) | 1.1707 | (.0001) | 1.1689 | (.0002) | 1.1733 | (.0001) | 1.2038 | (.0001) |
| 3 | 1.185 | (.006) | 1.1808 | (.0005) | 1.1817 | (.0001) | 1.1951 | (.0005) | 1.1747 | (.0023) |
| 4 | 1.178 | (.005) | 1.1739 | (.0007) | 1.1829 | (.0001) | 1.1903 | (.0015) | 1.1640 | (.0008) |
| 5 | 1.183 | (.007) | 1.1824 | (.0004) | 1.1899 | (.0003) | 1.1884 | (.0002) | 1.1832 | (.0001) |
| 6 | 1.168 | (.007) | 1.1675 | (.0001) | 1.1861 | (.0001) | 1.1914 | (.0038) | 1.1904 | (.0015) |
| 7 | 1.165 | (.006) | 1.1650 | (.0011) | 1.1823 | (.0003) | 1.1849 | (.0004) | 1.1807 | (.0008) |
| 8 | 1.186 | (.007) | 1.1967 | (.0011) | 1.1982 | (.0001) | 1.2092 | (.0005) | 1.1931 | (.0006) |
| 9 | 1.179 | (.006) | 1.1786 | (.0001) | 1.1922 | (.0002) | 1.2070 | (.0003) | 1.1734 | (.0008) |
| All Groups | 1.177 | (.011) | 1.180 | (.013) | 1.187 | (.010) | 1.196 | (.016) | 1.185 | (.013) |

Table 2b: Site 2

| 1 | 1.208 | (.012) | 1.2201 | (.0005) | 1.1930 | (.0016) | 1.2138 | (.0008) | 1.2014 | (.0006) |
|---|---|---|---|---|---|---|---|---|---|---|
| 2 | 1.172 | (.004) | 1.1687 | (.0002) | 1.1684 | (.0010) | 1.1927 | (.0008) | 1.2274 | (.0022) |
| 3 | 1.185 | (.005) | 1.1877 | (.0012) | 1.1969 | (.0002) | 1.2121 | (.0014) | 1.2047 | (.0023) |
| 4 | 1.177 | (.006) | 1.1702 | (.0001) | 1.1814 | (.0007) | 1.2187 | (.0003) | 1.1928 | (.0003) |
| 5 | 1.183 | (.009) | 1.1785 | (.0009) | 1.1900 | (.0002) | 1.1911 | (.0005) | 1.1953 | (.0010) |
| 6 | 1.176 | (.007) | 1.1764 | (.0001) | 1.1703 | (.0010) | 1.1909 | (.0004) | 1.1855 | (.0004) |
| 7 | 1.171 | (.007) | 1.1704 | (.0003) | 1.1745 | (.0008) | 1.1891 | (.0012) | 1.1833 | (.0015) |
| 8 | 1.192 | (.009) | 1.1980 | (.0031) | 1.1938 | (.0003) | 1.2184 | (.0008) | 1.2156 | (.0010) |
| 9 | 1.175 | (.005) | 1.1782 | (.0002) | 1.1812 | (.0001) | 1.2138 | (.0005) | 1.1952 | (.0006) |
| All Groups | 1.181 | (.013) | 1.183 | (.016) | 1.183 | (.010) | 1.205 | (.013) | 1.200 | (.014) |

Table 2c: Site 3 (Central site)

| 1 | 1.219 | (.014) | 1.2332 | (.0004) | 1.1810 | (.0016) | 1.1956 | (.0016) | 1.1946 | (.0024) |
|---|---|---|---|---|---|---|---|---|---|---|
| 2 | 1.182 | (.006) | 1.1771 | (.0006) | 1.1524 | (.0003) | 1.1782 | (.0004) | 1.1943 | (.0011) |
| 3 | 1.199 | (.008) | 1.1864 | (.0030) | 1.1830 | (.0013) | 1.2037 | (.0019) | 1.1926 | (.0012) |
| 4 | 1.191 | (.009) | 1.1800 | (.0001) | 1.1738 | (.0003) | 1.2097 | (.0008) | 1.1933 | (.0003) |
| 5 | 1.192 | (.011) | 1.1883 | (.0001) | 1.1890 | (.0001) | 1.1817 | (.0008) | 1.1900 | (.0010) |
| 6 | 1.183 | (.007) | 1.1844 | (.0003) | 1.1632 | (.0008) | 1.1995 | (.0007) | 1.1859 | (.0005) |
| 7 | 1.182 | (.009) | 1.1786 | (.0003) | 1.1631 | (.0005) | 1.1691 | (.0002) | 1.1639 | (.0003) |
| 8 | 1.207 | (.008) | 1.2120 | (.0006) | 1.1831 | (.0004) | 1.2237 | (.0002) | 1.2237 | (.0005) |

TABLE 2-continued

Mean (SD) tissue hydration index, pooled pre-elevation measurements,
immediately pre-elevation (t = 0) and at 1, 6 and 12 h post flap elevation.
* = pooled measurements for the 72 pre-operative h for which control measurements
were obtained

| TIME (h.) | Pre-Op* | | 0 | | 1 | | 6 | | 12 | |
|---|---|---|---|---|---|---|---|---|---|---|
| ANIMAL # | Means | (SD) | Means | (SD) | Means | (SD) | Means | (SD) | Means | (SD) |
| 9 | 1.189 | (.013) | 1.2073 | (.0005) | 1.1743 | (.0005) | 1.2186 | (.0006) | 1.2186 | (.0002) |
| All Groups | 1.193 | (.015) | 1.194 | (.018) | 1.174 | (.011) | 1.198 | (.018) | 1.191 | (.012) |

Table 2d: Site 4

| 1 | 1.212 | (.017) | 1.2220 | (.0007) | 1.1508 | (.0008) | 1.2151 | (.0006) | 1.1894 | (.0006) |
| 2 | 1.182 | (.008) | 1.1749 | (.0004) | 1.1150 | (.0001) | 1.1459 | (.0003) | 1.1893 | (.0012) |
| 3 | 1.202 | (.004) | 1.1957 | (.0024) | 1.1792 | (.0003) | 1.1776 | (.0013) | 1.1231 | (.0002) |
| 4 | 1.197 | (.008) | 1.1891 | (.0002) | 1.1677 | (.0001) | 1.2460 | (.0017) | 1.1968 | (.0009) |
| 5 | 1.194 | (.014) | 1.1842 | (.0004) | 1.1718 | (.0003) | 1.1819 | (.0010) | 1.1881 | (.0010) |
| 6 | 1.190 | (.006) | 1.1909 | (.0003) | 1.1683 | (.0005) | 1.1352 | (.0017) | 1.1039 | (.0008) |
| 7 | 1.174 | (.011) | 1.1759 | (.0002) | 1.1496 | (.0002) | 1.1905 | (.0008) | 1.1574 | (.0004) |
| 8 | 1.214 | (.011) | 1.2275 | (.0017) | 1.1998 | (.0012) | 1.1881 | (.0012) | 1.1239 | (.0007) |
| 9 | 1.198 | (.009) | 1.2042 | (.0001) | 1.1663 | (.0003) | 1.2189 | (.0011) | 1.1886 | (.0015) |
| All Groups | 1.196 | (.016) | 1.196 | (.018) | 1.163 | (.023) | 1.189 | (.034) | 1.162 | (.035) |

Table 2e: Site 5 (Distal site)

| 1 | 1.190 | (.013) | 1.1925 | (.0004) | 1.1160 | (.0009) | 1.0744 | (.0008) | 1.0614 | (.0005) |
| 2 | 1.171 | (.006) | 1.1714 | (.0003) | 1.1159 | (.0004) | 1.0602 | (.0001) | 1.0439 | (.0001) |
| 3 | 1.197 | (.005) | 1.1907 | (.0007) | 1.1577 | (.0005) | 1.0999 | (.0002) | 1.0797 | (.0004) |
| 4 | 1.185 | (.012) | 1.1662 | (.0001) | 1.1545 | (.0011) | 1.0880 | (.0006) | 1.0622 | (.0013) |
| 5 | 1.186 | (.012) | 1.1787 | (.0002) | 1.1512 | (.0002) | 1.1114 | (.0001) | 1.0904 | (.0003) |
| 6 | 1.164 | (.006) | 1.1681 | (.0002) | 1.1425 | (.0007) | 1.0848 | (.0025) | 1.0795 | (.0008) |
| 7 | 1.182 | (.005) | 1.1882 | (.0007) | 1.1760 | (.0024) | 1.1241 | (.0002) | 1.0859 | (.0001) |
| 8 | 1.203 | (.005) | 1.2005 | (.0007) | 1.1767 | (.0004) | 1.1124 | (.0007) | 1.0820 | (.0015) |
| 9 | 1.188 | (.011) | 1.2016 | (.0050) | 1.1952 | (.0010) | 1.1108 | (.0013) | 1.0609 | (.0042) |
| All Groups | 1.186 | (.015) | 1.184 | (.013) | 1.154 | (.026) | 1.096 | (.020) | 1.072 | (.015) |

TABLE 3

Spearman ranked correlation coefficients between the wavelength channels
of multispectral radiance image averaged over the four reversed McFarlane
skin flaps. Bracketed figures represent the standard deviation in the
calculated correlation coefficient over the four skin flaps.

| λ (nm) | 430 | 550 | 565 | 760 | 830 |
|---|---|---|---|---|---|
| 430 | — | — | — | — | — |
| 550 | 0.88 (0.02) | — | — | — | — |
| 565 | 0.86 (0.04) | 0.96 (0.02) | — | — | — |
| 760 | 0.51 (0.11) | 0.66 (0.03) | 0.68 (0.04) | — | — |
| 830 | 0.31 (0.13) | 0.49 (0.08) | 0.51 (0.12) | 0.85 (0.04) | — |
| 980 | 0.37 (0.15) | 0.42 (0.11) | 0.42 (0.08) | 0.61 (0.02) | 0.73 (0.04) |

TABLE 4a

Percent variance accounted for the principal components of the
multispectral reflectance image and the corresponding wavelength loadings for each
of the principal components. The mean values (standard deviation is reported in
brackets) for the four McFarlane skin flaps are reported.

| | | Wavelength loadings | | | | | |
|---|---|---|---|---|---|---|---|
| PC# | % variance | 430 | 550 | 565 | 760 | 830 | 980 |
| 1 | 73.53(5.99) | 0.72(0.06) | −0.10(0.04) | −0.16(0.02) | −0.31(0.01) | −0.31(0.03) | 0.49(0.11) |
| 2 | 20.29(4.57) | 0.43(0.09) | 0.32(0.01) | 0.29(0.05) | −0.04(0.06) | −0.34(0.05) | −0.70(0.04) |
| 3 | 3.04(2.35) | 0.24(0.37) | −0.48(0.03) | −0.41(0.04) | 0.23(0.44) | 0.18(0.39) | −0.31(0.04) |
| 4 | 1.99(0.79) | 0.00(0.23) | −0.09(0.13) | −0.07(0.14) | 0.46(0.46) | −0.31(0.72) | 0.29(0.09) |
| 5 | 0.61(1.22) | 0.17(0.28) | 0.41(0.05) | 0.43(0.06) | 0.13(0.635) | 0.36(0.16) | 0.29(0.09) |
| 6 | 0.53(0.21) | −0.03(0.05) | 0.68(0.03) | −0.72(0.02) | 0.06(0.12) | 0.03(0.10) | −0.01(0.02) |

TABLE 4b

Average wavelength loadings of the varimax rotated factors derived the first 3 principal components of the multispectral reflectance image. Bracketed figures represent the standard deviation in the varimax factor loadings over the four McFarlane skin flaps.

| | | | Wavelength loadings | | | |
|---|---|---|---|---|---|---|
| RF* | 430 | 550 | 565 | 760 | 830 | 980 |
| 1 | 0.93(0.02) | −0.06(0.16) | −0.10(0.17) | −0.09(0.05) | −0.25(0.05) | −0.01(0.08) |
| 2 | 0.01(0.07) | 0.14(0.01) | 0.17(0.04) | 0.19(0.19) | −0.05(0.23) | −0.92(0.02) |
| 3 | −0.01(0.02) | −0.55(0.02) | −0.46(0.06) | 0.22(0.48) | 0.31(0.46) | 0.02(0.02) |

*RF = rotated factors

What is claimed is:

1. A non-invasive method of assessing tissue viability of a patient comprising:
   accessing a portion of tissue of the patient wherein the communication of fluids between the portion and a main body of the patient is compromised such that the viability of the tissue portion is in question;
   locating a probe at the tissue portion;
   collecting with the probe a spectrum of visible and near infra-red light from said tissue portion;
   analyzing said spectrum to generate data related to the viability of the tissue portion;
   and using the data from said spectrum to make a determination of the viability of the tissue portion,
   wherein sufficient spectral points and data are collected so that the determination of the viability of the tissue portion be solely made from said spectrum.

2. The method according to claim 1 wherein the tissue portion forms a portion of the body which is damaged.

3. The method according to claim 2 wherein the damage is caused by burning.

4. The method according to claim 1 wherein the spectrum is collected in the absence of added metabolic substrate.

5. The method according to claim 1 wherein the tissue portion is attached to the main body portion by rejoining severed blood vessels, thereby compromising the communication of fluid from the main body portion to the tissue portion.

6. The method according to claim 1 wherein the data related to the viability of the tissue portion comprises data on oxygenation of the tissue portion.

7. The method according to claim 6 wherein the data on the oxygenation of the tissue portion comprises comparing levels of deoxyhemoglobin and oxyhemoglobin.

8. The method according to claim 7 wherein the levels of deoxyhemoglobin and oxyhemoglobin are compared by measuring the ratio of absorbance at a wavelength between 790–810 nm to absorbance at a wavelength between 740–780 nm.

9. The method according to claim 1 including the steps of removing the probe, subsequently relocating the probe proximal to the tissue portion, collecting from the probe a second spectrum of visible and near infra-red light from the tissue portion, analyzing the second spectrum to generate data related to the viability of the tissue portion and using the data from the second spectrum to make a determination of the viability of the tissue portion.

10. The method according to claim 1 wherein the data related to the viability of the tissue portion comprises data on both hydration and oxygenation of the tissue portion.

11. The method according to claim 10 wherein the data on the oxygenation of the tissue is obtained by measuring the ratio of absorbance at a wavelength between 790–810 nm to absorbance at a wavelength between 740–780 nm and the data on the hydration of the tissue portion is obtained by measuring the ratio of absorbance at a wavelength between 960–1080 nm to absorbance at 900 nm.

12. The method according to claim 1 wherein the probe is located at least 1 mm away from the tissue portion.

13. A non-invasive method of assessing tissue viability of a patient comprising:
   accessing a damaged portion of tissue of the patient wherein the communication of fluids between the tissue portion and a main body of the patient is compromised such that the viability of the tissue portion is in question, wherein the tissue portion has been or is suspected of having been damaged by freezing;
   locating a probe at the tissue portion;
   collecting with the probe a spectrum of visible and near infra-red light from said tissue portion;
   analyzing said spectrum to generate data related to the viability of the tissue portion:
   and using the data from said spectrum to make a determination of the viability of the tissue portion,
   wherein sufficient spectral points and data are collected so that the determination of the viability of the tissue portion can be made from said spectrum.

14. A non-invasive method of assessing tissue viability of a patient comprising:
   accessing a damaged portion of tissue of the patient wherein the communication of fluids between the tissue portion and a main body of the patient is compromised such that the viability of the tissue portion is in question;
   locating a probe at the tissue portion;
   collecting with the probe a spectrum of visible and near infra-red light from said tissue portion;
   analyzing said spectrum to measure water content of the tissue portion by measuring the ratio of absorbance at a wavelength between 960–1080 nm to absorbance at 900 nm; and
   determining of the viability of the tissue portion based on the water content of the tissue portion.

15. The method according to claim 14 including:
   measuring the ratio of absorbance at a wavelength between 790–810 nm to absorbance at a wavelength between 740–780 nm to determine the oxygenation of the tissue portion; and
   determining viability of the tissue portion based on the water content and oxygenation of the tissue portion.

16. A non-invasive method of assessing tissue viability of a patient comprising:

accessing a portion of tissue of the patient wherein the communication of fluids between the portion and a main body of the patient is compromised such that the viability of the tissue portion is in question;

locating a probe at least 1 mm away from the tissue portion;

collecting with the probe a spectrum of visible and near infra-red light from said tissue portion;

analyzing said spectrum to generate data related to the viability of the tissue portion;

and using the data from said spectrum to make a determination of the viability of the tissue portion, wherein sufficient spectral points and data are collected so that the determination of the viability of the tissue portion can be solely made from said spectrum.

* * * * *